United States Patent
Petri et al.

(10) Patent No.: US 9,841,685 B2
(45) Date of Patent: Dec. 12, 2017

(54) DETERMINATION OF A CORRECTED VARIABLE

(71) Applicant: Carl Zeiss SMT GmbH, Oberkochen (DE)

(72) Inventors: Christoph Petri, Oberkochen (DE); Christian Wald, Aalen (DE); Daniel Runde, Oberkochen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 0 days.

(21) Appl. No.: 15/353,406

(22) Filed: Nov. 16, 2016

(65) Prior Publication Data

US 2017/0068166 A1 Mar. 9, 2017

Related U.S. Application Data

(63) Continuation of application No. PCT/EP2015/060770, filed on May 15, 2015.

(30) Foreign Application Priority Data

May 16, 2014 (DE) .................... 10 2014 209 348

(51) Int. Cl.
*G01N 21/88* (2006.01)
*G03F 7/20* (2006.01)
(Continued)

(52) U.S. Cl.
CPC ......... *G03F 7/706* (2013.01); *G01N 21/8851* (2013.01); *G01N 21/956* (2013.01);
(Continued)

(58) Field of Classification Search
CPC . G01M 11/02; G03F 7/06; G03F 1/84; G01N 21/8851; G01N 21/956; G01N 2021/95676
(Continued)

(56) References Cited

U.S. PATENT DOCUMENTS 7,088,458 B1 * 8/2006 Wegmann .................. G01J 9/02
356/124
7,333,216 B2 * 2/2008 Wegmann .................. G01J 9/02
356/124
(Continued)

FOREIGN PATENT DOCUMENTS

DE 102009038558 A1 3/2011
DE 102010062763 A1 6/2012
DE 102012111008 A1 5/2014

OTHER PUBLICATIONS

International Search Report and Written Opinion in counterpart International Application No. PCT/EP2015/060770, dated Oct. 21, 2015.

*Primary Examiner* — Hoa Pham
(74) *Attorney, Agent, or Firm* — Edell, Shapiro & Finnan, LLC

(57) ABSTRACT

A method for determining a corrected variable, which depends on at least one parameter, in a parameter range of the parameter, includes carrying out a measurement, measurement values of the variable being made available in a plurality of separate and non-overlapping subranges of the parameter range; correcting measurement values of the variable using an approximation, in which measurement values of the variable are approximated with a smooth function and with subrange functions of the subranges of the parameter range. The smooth function allows reproduction of the progression of the variable over the parameter range. The subrange functions permit an individual change of the variable in the subranges. Also disclosed are methods for adjusting imaging optics of an optical system, devices for determining a corrected variable, which depends on at least one parameter in a parameter range, and methods for determining a plurality of corrected wavefront errors in an image field.

19 Claims, 7 Drawing Sheets

(51) Int. Cl.
 *G03F 1/84* (2012.01)
 *G01N 21/956* (2006.01)
(52) U.S. Cl.
 CPC .............. *G03F 1/84* (2013.01); *G03F 7/7085* (2013.01); *G03F 7/70591* (2013.01); *G01N 2021/95676* (2013.01)
(58) Field of Classification Search
 USPC ........................... 356/121–127, 237.1–237.5
 See application file for complete search history.

(56) References Cited

U.S. PATENT DOCUMENTS

| | | | |
|---|---|---|---|
| 8,913,120 B2* | 12/2014 | Poortinga | G03F 1/144 348/79 |
| 2011/0090329 A1 | 4/2011 | Poortinga et al. | |
| 2013/0271749 A1 | 10/2013 | Korb et al. | |
| 2013/0301024 A1* | 11/2013 | Conradi | G03F 7/70483 355/67 |
| 2014/0347721 A1* | 11/2014 | Bittner | G03F 7/70191 359/351 |
| 2015/0260504 A1 | 9/2015 | Schoenleber et al. | |
| 2016/0202118 A1* | 7/2016 | Ehrmann | G03F 7/70133 250/252.1 |

* cited by examiner

DETERMINATION OF A CORRECTED VARIABLE

CROSS REFERENCE TO RELATED APPLICATIONS

This is a Continuation of International Application PCT/EP2015/060770, which has an international filing date of May 15, 2015, and the disclosure of which is incorporated in its entirety into the present Continuation by reference. The following disclosure is also based on and claims the benefit of and priority under 35 U.S.C. §119(a) to German Patent Application No. DE 10 2014 209 348.1, filed May 16, 2014, which is also incorporated in its entirety into the present Continuation by reference.

FIELD OF THE INVENTION

The invention relates to a method and an apparatus for establishing a corrected variable which depends on at least one parameter, in a parameter range of the at least one parameter. The invention furthermore relates to a method for adjusting an imaging optical unit of an optical system and to a method for establishing a plurality of corrected wavefront aberrations in an image field.

BACKGROUND

With a measurement, measurement values in a parameter range of interest of the at least one parameter may be provided for a variable which depends on at least one parameter. Depending on the scope of the parameter range and the accuracy of the measurement, carrying out the measurement in the whole parameter range may be connected with much outlay and with high costs of a measuring device used for the measurement. This may be avoided by virtue of only obtaining measurement values of the variable in subregions of the parameter range. These may be disjoint, i.e. separate and non-overlapping, subregions.

By way of example, such a procedure may be considered in an optical inspection system, which serves to examine an object, e.g. a lithography mask or reticle. The inspection system may comprise an illumination source for illuminating the object arranged in an object plane with radiation and an imaging optical unit. It is possible to image an object field into an image field of an image plane with the imaging optical unit. It is possible to use a sensor arranged in the image plane for radiation measurement purposes.

In the inspection system, it may be of interest to identify an imaging or wavefront aberration in the image field that is caused by the imaging optical unit. Here, the wavefront aberration constitutes the aforementioned variable and the image field constitutes the parameter range, in the present case with two parameters in the form of spatial coordinates. Instead of carrying out the radiation measurement for providing measurement values of the imaging aberration in the entire image field, the measurement may relate to disjoint subregions or partial fields of the image field. By way of example, this may be realized by virtue of a sensor used for the measurement being successively arranged at different measurement positions. In so doing, a plurality of partial measurements are carried out in succession with the sensor and the sensor is moved to the individual measurement positions therebetween. A radiation measurement with a sensor which has partial sensors with non-overlapping detection regions is also possible.

A consequence of providing measurement values of a variable in a plurality of, or disjoint, subregions of a parameter range may be that the measurement values of the variable are afflicted by measurement errors in the individual subregions, said measurement errors only occurring individually in the corresponding subregions. A varying measurement error may be present from subregion to subregion. Such a falsification of the measurement values of the variable has an adverse effect on the significance thereof.

In view of the above-described inspection system, establishing a wavefront aberration may serve to determine adjustment processes for adjusting the imaging optical unit in order to reduce the imaging aberration thereof. The use of a sensor at different measurement positions may be accompanied by incorrect positioning of the sensor. This may lead to measurement values of the wavefront aberration being respectively afflicted with a constant measurement error (offset) in individual subregions of the image field. The offset error could be significantly greater than other measurement errors and, in particular, greater than the field variation of the wavefront aberration caused by the imaging optical unit. This makes it more difficult to determine suitable adjustment processes. Such a disadvantage may correspondingly occur when using a sensor with a plurality of non-overlapping partial sensors. Here, offset errors occurring in subregions of the image field may be a consequence of positional errors of the partial sensors.

SUMMARY

An object of the present invention consists of specifying a method and an apparatus, with which it is possible to carry out a reliable correction of measurement values of a variable, wherein the measurement values are obtained in subregions of a parameter range. A further object consists of specifying a cost-effective and reliable method for adjusting an imaging optical unit of an optical system. A further object consists of specifying a reliable method for establishing a plurality of corrected wavefront aberrations in an image field.

These objects are achieved by the features of the independent patent claims. Further advantageous embodiments of the invention are specified in the dependent claims.

In accordance with one aspect of the invention, a method is proposed for establishing a corrected variable which depends on at least one parameter, in a parameter range of the at least one parameter. The method comprises carrying out a measurement, wherein measurement values of the variable are provided in a plurality of separate and non-overlapping subregions of the parameter range. The method furthermore comprises carrying out a correction of measurement values of the variable using an approximation, in which measurement values of the variable are approximated by a smooth function and by subregion functions assigned to the subregions of the parameter range. A course of the variable is reproducible over the parameter range with the smooth function. An individual change of the variable is able to be caused in the subregions of the parameter range with the subregion functions.

In the method, measurement values of the variable, which relate to associated values of the at least one parameter, are provided in a plurality of disjoint subregions of the parameter range. This renders it possible to carry out the underlying measurement with little measurement outlay and with low costs. However, this procedure may be connected with an incorrect measurement, and so the measurement values of the variable in the individual subregions of the parameter range each may have their own measurement errors, which are independent of the other subregions.

What is exploited in the method for suppressing or correcting such measurement errors is that the actual variable, i.e. the variable not afflicted by measurement errors, may have corresponding regularities or predictable properties in relation to the parameter range and may consequently be described by a smooth function over the parameter range. In contrast thereto, such regularities are not found, or substantially not found, in the individual measurement errors in the subregions.

These circumstances are accounted for by the method by virtue of the measurement values of the variable being approximated both by a smooth function imaging the course of the variable over the parameter range and by subregion functions assigned to the subregions. Within the scope of the approximation, the subregion functions in each case allow an individual change of the variable to be caused in the associated subregions, i.e. independently of other subregions. In this way, it is possible to reproduce the effect of an incorrect measurement of the variable in the relevant subregions and hence reproduce the occurrence of the measurement errors with the subregion functions. As a consequence, an accurate approximation to the measurement values of the variable with a small or minimal deviation may be obtained with the smooth function and the subregion functions.

The individual change of the variable in the individual subregions of the parameter range, which is able to be caused with the subregion functions, is not only used for the approximation, but also serves as a basis for the correction. Here, individual measurement errors in the individual subregions may be suppressed, i.e. eliminated, or reduced at least in part or to a substantial extent. It is therefore possible to provide a corrected or reconstructed variable in the parameter range, said variable being able to come close to the actual variable, possibly up to a difference in the form of a constant global offset value.

Reference is made to the fact that the phrase "actual" or "actual variable", as employed here, relates to the variable without measurement error, and hence to a variable which is able to be provided within the scope of an idealized measurement without the input of measurement errors in the subregions of the parameter range.

Further possible embodiments and details of the method are described below.

For the purposes of carrying out the approximation, provision is made in accordance with one embodiment for the parameter range to be discretized into a finite number of nodes. In this way, the method may be carried out using a suitable evaluation device.

The variable may be dependent on one parameter, but also on a plurality of parameters, e.g. two parameters. In such an embodiment, the parameter range comprises the plurality of parameters and the measurement values of the variable relate to associated parameter values of the plurality of parameters.

The at least one parameter is a spatial coordinate in a further embodiment. By way of example, the parameter range may comprise two parameters in the form of spatial coordinates. The two spatial coordinates may be e.g. coordinates of a two-dimensional orthogonal coordinate system. By way of example, the parameter range may represent an image field in such a configuration. Here, the measurement values of the variable may relate to field points or image points of the image field with associated image point coordinates.

Other parameters may also be used in the method. By way of example, the at least one parameter may be a time. A further example is a parameter range comprising a time and one or more spatial coordinates.

In a further embodiment, the variable is in each case modifiable by the same value in the associated subregions with the subregion functions. This embodiment may be used if constant or substantially constant measurement errors (offsets) are present in the subregions of the parameter range, said constant measurement errors afflicting all measurement values of the variable in the relevant subregions. By using the subregion functions with the aforementioned property, it is possible to reproduce the effect of the offset errors and, as a consequence, reliably reconstruct mean values of the variable in the subregions of the parameter range. Expressed differently, it is possible to suppress the constant or the substantially constant falsification of measurement values of the variable as a consequence of measurement errors, said falsification being individually present in the subregions.

The smooth function used in the method may have a plurality of basis functions. By way of example, the smooth function may be a polynomial function. It is possible to use simple polynomial basis functions.

In a further embodiment, the correction comprises forming corrected values of the variable. In so doing, error-afflicted measurement values of the variable may be replaced by the corresponding corrected values of the variable. The corrected values of the variable, which may also be referred to as reconstructed values, may come close to the actual, i.e. non-measurement-error-afflicted, values of the variable and substantially correspond to the latter.

In a further embodiment, the approximation comprises determining coefficients of the subregion functions. Moreover, measurement values of the variable are corrected using the coefficients of the subregion functions. In this way, it is possible to form corrected values of the variable, through which, as described above, error-afflicted measurement values of the variable may be replaced. Entries or weightings of the subregion functions, and hence a strength of measurement errors in the individual subregions, may be reproduced by way of the coefficients of said subregion functions. Therefore, the use of the coefficients of the subregion functions renders it possible to rectify or suppress measurement errors in a reliable manner. In so doing, it is possible to reliably reconstruct mean values of the variable in the subregions of the parameter range.

In relation to the use of coefficients of the subregion functions, it is furthermore possible to use the following configurations of the method.

In a further embodiment, the approximation comprises forming a function matrix from subregion functions and basis functions of the smooth function, forming the pseudo-inverse of the function matrix, and multiplying the pseudo-inverse of the function matrix by a vector of measurement values of the variable to form a coefficient vector. The coefficient vector comprises coefficients of the subregion functions and coefficients of the basis functions of the smooth function. With the aforementioned steps, it is possible to meet the demand for an approximation to the measurement values of the variable by the smooth function and the subregion functions with minimal deviation. As a result of this, it is possible to provide the coefficients of the subregion functions, with which it is possible to correct measurement values of the variable, in a reliable manner. The correction may be carried out as described below.

In a further embodiment, the correction comprises multiplying a matrix of subregion functions by a vector of coefficients of the subregion functions (established via the approximation) to form a product and subtracting the product, apart from the mean value thereof, from the vector of measurement values of the variable. By way of this procedure it is possible to form corrected values of the variable which may substantially correspond to the actual variable. The product may relate to the entries or weightings of all approximated subregion functions. The associated mean value may also be referred to as constant component. The phrase "apart from the mean value thereof" may be satisfied by virtue of the mean value of the product being subtracted from the product and this term being subtracted from the vector of measurement values of the variable.

By subtracting the mean value of the product, it is possible to ensure that it is predominantly relative differences, i.e. differences present from subregion to subregion of the parameter range, in the measurement values of the variable that are corrected and that there is substantially no global or uniform variable correction over all subregions. As a result, the corrected values of the variable may come close to the actual variable.

In a further embodiment, subregion functions with a zero mean value are used. These are subregion functions which, in relation to the parameter range, have a mean value of zero. Such subregion functions may be formed by virtue of the respectively associated mean value being subtracted from each subregion function with a mean value. If use is made of subregion functions with the zero mean value, the above-described subtraction of the mean value of the product (mean value of all entries of the subregion functions) is implicitly contained in the approximation and correction. When use is made of subregion functions with a zero mean value, the mean value of the product has the value of zero, and so a subtraction of same may also be dispensed with. Thus, in relation to the above-described correction step, it is possible to merely subtract the product from the vector of measurement values of the variable, provided that subregion functions with a zero mean value are used in the other steps.

A further advantage of using subregion functions with a zero mean value consists of the approximation of the measurement values of the variable being able to be carried out uniquely. In contrast thereto, the mean value of the entries of the subregion functions may, in the case of subregion functions with a mean value, be included twice in the used set of functions or in the function matrix, to be precise as a constant in the smooth function and as a sum of the subregion functions. This may have a non-unique approximation as a consequence.

As specified above, a polynomial function which may comprise simple polynomial basis functions may be used as smooth function. For the purposes of the regularization, and hence improvement of the approximation, use may furthermore be made of a smooth function which comprises orthogonalized or orthonormalized basis functions. The use of a polynomial function with normalized polynomial basis functions is also possible.

In a further embodiment, the approximation and correction are carried out together, by virtue of a function matrix being formed from subregion functions and basis functions of the smooth function, the pseudoinverse of the function matrix being formed, a partial matrix being formed from the pseudoinverse of the function matrix, with coefficients of the subregion functions being generable by way of the partial matrix, a matrix of subregion functions being multiplied by the partial matrix to form a product, the product being subtracted from an identity matrix to form a correction matrix, and the correction matrix being multiplied by a vector of measurement values of the variable. This embodiment, with which corrected values of the variable may be formed in a simple manner, likewise meets the demand of obtaining an approximation to the measurement values of the variable with a minimum deviation. In so doing, the approximation and correction are based on a simple multiplication of measurement values of the variable by the correction matrix. In this context, it is furthermore possible to use the correction matrix, formed once, to correct measurement values of the variable, which are obtained with various measurements, in each case.

As specified above, the method may be carried out in such a way that corrected values of the variable are formed. In a further embodiment, which is able to be carried out additionally or alternatively, the correction comprises forming an approximated course of the variable. The approximated course of the variable may come close to the actual, i.e. non-measurement-error-afflicted, variable and substantially correspond to the latter. It is possible to replace the measurement values of the variable by the approximated course of the variable. By way of example, in this way, it is possible to reconstruct a course of the variable over the whole parameter range of interest. Forming the approximated course of the variable facilitates an elimination of spot noise.

Furthermore, interpolation and/or extrapolation may occur within the scope of the correction. To this end, a further embodiment proposes that the correction comprises forming at least one complementary value of the variable, wherein the complementary value of the variable belongs to a value of the at least one parameter, for which no measurement value of the variable is available. The provision of the at least one complementary value of the variable may be carried out on the basis of an approximated course of the variable.

An approximated course of the variable may be formed with the embodiment described below, in which the approximation and correction are likewise carried out together. To this end, provision is made of forming a function matrix from subregion functions and basis functions of the smooth function, forming the pseudoinverse of the function matrix, forming a partial matrix from the pseudoinverse of the function matrix, with coefficients of the basis functions of the smooth function being generable by way of the partial matrix, multiplying a matrix of basis functions of the smooth function by the partial matrix to form a course generation matrix, and multiplying the course generation matrix by a vector of measurement values of the variable. This embodiment, with which an approximated course of the variable may be formed in a simple manner, likewise satisfies the demand of obtaining an approximation to the measurement values of the variable with a minimum deviation. In so doing, the approximation and correction are based on a simple multiplication of measurement values of the variable by the course generation matrix. It is possible to use the course generation matrix, formed once, to form approximated courses of the variable of measurement values of the variable, which are obtained with various measurements, in each case.

In one development of the method, the measurement carried out in the method relates to a plurality of separate, non-overlapping subregions and, additionally, at least one further subregion of the parameter range which overlaps with at least one of the separate, non-overlapping subregions. Different configurations may be considered in relation to this method variant.

By way of example, it is possible that at least one subregion of the disjoint subregions considered in the method is a unified subregion, for which common measurement values of the variable are provided. Such a unified subregion may be composed of overlapping subregions. Common measurement values of the variable of interest may be provided on the basis of suitable preprocessing or correction of measurement values initially obtained in the individual overlapping subregions. By way of example, a stitching method may be carried out to this end. Subsequently, the unified subregion and the associated common measurement values may be used in the correction or approximation carried out with the smooth function and the subregion functions. Here, a corresponding subregion function may be assigned to the unified subregion and the correction procedure may be carried out as described above or in accordance with one of the above-described embodiments (e.g. forming corrected values of the variable, determining and using coefficients of the subregion functions for correction purposes, using the pseudoinverse of the function matrix, of the correction matrix, of the course generation matrix, etc.). The subregion function assigned to the unified subregion is selected in such a way that, therewith, an individual modification of the variable is able to be caused or the variable is in each case modifiable by the same value in the subregion.

It is also possible to form a plurality of unified subregions, provide measurement values therefor, and take these into account in the correction and approximation. This case may be considered if the measurement relates to a plurality of further subregions which overlap with other subregions.

In a further embodiment of the method, in which measurement values of the variable are provided in at least one further subregion of the parameter range, wherein the further subregion overlaps with at least one of the separate and non-overlapping subregions, the approximation is carried out with a further subregion function assigned to the further subregion, with which further subregion function an individual change of the variable is able to be caused in the further subregion of the parameter range. The further subregion function may be selected in such a way that, herewith, the variable of interest is modifiable by the same value in the relevant subregion in each case. In the case of a plurality of further subregions, a plurality of further subregion functions may be used in a corresponding manner.

Hence, in comparison with the variants described above, there is no preprocessing or union of subregions. Instead, a further overlapping subregion is treated like the remaining subregions. Here, the correction procedure may be carried out as described above or in accordance with one of the above-described embodiments (e.g. forming corrected values of the variable, determining and using coefficients of the subregion functions for correction purposes, using the pseudoinverse of the function matrix, of the correction matrix, of the course generation matrix, etc.). In this configuration, there may be a double approximation in an overlap range of overlapping subregions or a multiple approximation in the case of more than two overlapping subregions.

The method or the various embodiments thereof may be used in view of different variables. By way of example, an optical variable comes into consideration. Here, the parameter range may comprise two spatial coordinates and represent an image field.

By way of example, the optical variable may be a distortion variable, with which it is possible to reproduce a distortion occurring in an image field, e.g. a pincushion-shaped or barrel-shaped distortion. With the method, it is possible to correct error-afflicted measurement values of the distortion variable as specified above, said measurement values being obtained in a plurality of, or disjoint, subregions of the image field. By way of example, in this case it may be possible to consider reconstructing the distortion over the whole image field, for example by virtue of an approximated course of the distortion variable being formed over the image field and/or complementary values of the variable being formed for the purposes of interpolation and/or extrapolation.

A further example of an optical variable is a wavefront aberration. By way of example, the wavefront aberration may be present in the form of a coefficient for a Zernike polynomial of a wavefront expansion. By way of example, this may be a distortion-reproducing or a—possibly local—image-offset-reproducing Zernike coefficient for Zernike polynomial Z2 or Z3 or a focal-offset-reproducing Zernike coefficient for Zernike polynomial Z4. The Zernike polynomials Z2, Z3, Z4 considered here are Zernike polynomials according to Noll's indices. The method may be used in order to correct error-afflicted measurement values of the wavefront aberration, which are provided in disjoint subregions of an image field, as described above.

In relation to an optical variable, provision is made in accordance with a further embodiment for the measurement to be a radiation measurement carried out with a spatially resolving sensor. By way of example, the spatially resolving sensor may be an electronic sensor with a multiplicity of radiation-sensitive sensor elements or pixels. By way of example, the sensor may be realized in the form of a CCD (charge-coupled device) sensor with radiation-sensitive photodiodes. After appropriate further processing or evaluating, measurement signals of the sensor are able to be converted into spatially dependent measurement values of the optical variable, which relate to image points of an image field.

The provision of measurement values of the optical variable at image points in several and/or disjoint subregions of an image field using a spatially resolving sensor may be implemented in different ways. By way of example, it may be considered to arrange the sensor at different measurement positions for the measurement. In so doing, a plurality of partial measurements are carried out in succession with the sensor and the sensor is moved to the individual measurement positions therebetween. In such a procedure, measurement errors, through which measurement values of the optical variable may be falsified to a different extent in individual subregions of the image field, may be a consequence of incorrect positioning of the sensor.

For the measurement, it is also possible to use a spatially resolving sensor which has a plurality of partial sensors with non-adjacent and non-overlapping detection regions. This way, it is also possible to provide measurement values of the optical variable at image points in disjoint subregions of an image field. Here, measurement errors, by which measurement values of the optical variable may be falsified to a different extent in individual subregions of the image field, may be a consequence of position errors of partial sensors of the sensor.

In addition to an electronic sensor or a CCD sensor, use may also be made of other spatially resolving sensors. An example is a sensor which has a light-sensitive layer, e.g. a photographic plate or a film. After measuring the radiation or exposing the light-sensitive layer, there may be a development of same and spatially dependent measurement values of the optical variable may be provided at image points of an image field within the scope of an analysis of the layer.

By way of example, measurement values of the optical variable may be provided in disjoint subregions of the image field by virtue of the analysis only relating to subregions of the layer, the layer only being irradiated in subregions, or a layer subdivided into subregions being used.

Instead of an optical variable, the method may also be used in relation to other variables measured in a plurality of, or disjoint, subregions of a parameter range. A possible example is a height or vertical extent of a test object. In this case, it may likewise be considered to provide corresponding spatially dependent measurement values in disjoint subregions of a two-dimensional image field with a measurement and correct measurement errors by carrying out the above-described method. By way of example, the height may be measured with an atomic force microscope or with a surface interferometer.

In accordance with a further aspect of the invention, a method for adjusting an imaging optical unit of an optical system is proposed. Here, the above-described method or the method configured in accordance with one of the above-described embodiments is carried out for establishing a corrected optical variable using a spatially resolving sensor which is able to be irradiated with radiation coming from the imaging optical unit. Furthermore, the imaging optical unit is adjusted on the basis of the corrected optical variable.

A cost-effective measurement is possible by the provision of measurement values of the optical variable in a plurality of, or disjoint, subregions of an image field, which, as specified above, may be carried out e.g. by a measurement with a sensor at different measurement positions or by using a sensor with a plurality of partial sensors. The correction of measurement errors accompanying this renders it possible to carry out the adjustment of the imaging optical unit with a high reliability and accuracy. Imaging properties of the imaging optical unit may be accurately reproduced with the corrected optical variable and, as a result thereof, said imaging properties may be taken account of, and optimized, within the scope of the adjustment. The influence of measurement errors, which leads to a falsification of measurement values of the optical variable, may be largely eliminated by the correction.

In view of the adjustment method, the smooth function, or the basis functions thereof, which is used in the approximation and correction may be set with knowledge of the optical properties of the imaging optical unit.

By way of example, establishing the corrected optical variable, on the basis of which the adjustment is carried out, may comprise forming corrected values of the optical variable. Additionally, or alternatively, provision may be made of forming an approximated course of the optical variable and/or forming at least one complementary value of the optical variable.

The spatially resolving sensor may, or may not, be a component of the optical system. In the second variant, the sensor may be used e.g. within the scope of a design of the optical system.

In relation to the radiation measurement carried out with the spatially resolving sensor, it may furthermore be considered to image one or more suitable test structures or marks, on the basis of which the spatially dependent measurement values of the optical variable may be provided, into the image field which is measured subregion-by-subregion or disjointly. For this purpose, use may be made of e.g. an object, e.g. a reticle, which has the test structure(s) and which is irradiated by the employed radiation. The radiation coming from the object, i.e. a transmitted or reflected radiation component, may be guided to the spatially resolving sensor by way of the imaging optical unit.

In accordance with a further aspect of the invention, an apparatus is proposed for establishing a corrected variable which depends on at least one parameter, in a parameter range of the at least one parameter. The apparatus comprises a measuring device, with which it is possible to provide measurement values of the variable in a plurality of separate and non-overlapping subregions of the parameter range. The apparatus furthermore comprises an evaluation device for correcting measurement values of the variable. The evaluation device is embodied to carry out the correction using an approximation, in which measurement values of the variable are approximated by a smooth function and by subregion functions assigned to the subregions. A course of the variable is reproducible over the parameter range with the smooth function. An individual change of the variable is able to be caused in the subregions of the parameter range with the subregion functions.

Measurement values of the variable may be provided in a plurality of disjoint subregions of the parameter range in the apparatus. Therefore, the measurement apparatus may have a cost-effective design. A possible effect connected herewith—that the measurement values of the variable respectively have individual measurement errors which are independent from other subregions in the individual subregions of the parameter range—may be suppressed by the correction with the evaluation device.

Reference is made to the fact that aspects and details described above with reference to the correction method and the adjustment method may also be used in the apparatus. In this context, reference is further made to the option of using the apparatus within the scope of the above-described adjustment of an imaging optical unit of an optical system.

Moreover, reference is made to the option of establishing a plurality of corrected variables in a common parameter range with the method and/or the apparatus. In so doing, measurement values of the plurality of variables may be provided in a plurality of, or disjoint, subregions of the parameter range and a dedicated separate error correction (with a dedicated approximation in each case), as described above, may be carried out for each one of the variables. By way of example, corrected values, an approximated course, and/or at least one complementary value may be provided for each one of the considered variables. By way of example, this may be considered for optical variables such as the above-described wavefront aberrations or coefficients for Zernike polynomials of a wavefront expansion.

Crosstalk between various variables may occur in the case of a plurality of variables of interest, in particular optical variables such as wavefront aberrations. Here, error causes for measurement or offset errors, which relate to a first variable, may also cause a measurement falsification of at least one further second variable. By way of example, incorrect positioning of a sensor, which causes measurement errors when measuring the coefficients for Zernike polynomial Z4, which reproduce a focal offset, also leads to measurement errors in relation to the Zernike coefficients for Zernike polynomial Z2 and/or Z3 reproducing an image offset.

The crosstalk may be suppressed by virtue of an additional correction of the second variable or measurement values of the second variable being carried out on the basis of an error correction of the first variable, which is carried out in accordance with the above approaches using an approximation. By way of example, the additional correction of the second variable may be carried out on the basis of coefficients of subregion functions which are determined within the scope of the error correction of the first variable. The additional correction of the second variable may be provided prior to, or after, an error correction of the second variable carried out in accordance with the above approaches using an approximation.

Moreover, reference is made to the possibility of using the method and/or the apparatus not only for suppressing offset errors but also for suppressing other measurement errors occurring individually in subregions of the parameter range. To this end, suitable subregion functions are used, with which the occurrence of such measurement errors in the subregions of the parameter range may be reproduced.

By way of example, in this context, the use of subregion functions may be considered, with all subregion functions or some, or a subgroup, of the subregion functions put together describing a smooth course over the parameter range. In order to facilitate a unique approximation in this case, it is conceivable to provide modified subregion functions, the sum of which equals zero, for all subregion functions or for the subset of the subregion functions. By way of example, this is possible by virtue of the scaled sum of all of these subregion functions being subtracted from each one of these subregion functions, with the scaling factor being the reciprocal of the number of these subregion functions. Further procedures for facilitating a unique approximation are conceivable as an alternative to modifying the subregion functions. By way of example, the associated coefficients of the subregion functions may be modified accordingly prior to forming the above-described product (product of the matrix of subregion functions with the vector of the coefficients of the subregion functions) provided for subtraction from the vector of measurement values of the considered variable.

Furthermore, the following procedure may be considered in view of a plurality of wavefront aberrations.

In accordance with a further aspect of the invention, a method is proposed for establishing a plurality of corrected wavefront aberrations which depend on two spatial coordinates, in an image field. The method comprises carrying out a radiation measurement with a spatially resolving sensor, wherein measurement values of the plurality of wavefront aberrations are provided in a plurality of separate and non-overlapping subregions of the image field. The method furthermore comprises carrying out a common correction of measurement values of the plurality of wavefront aberrations using an approximation, in which measurement values of the wavefront aberrations are approximated by a plurality of smooth functions assigned to the wavefront aberrations and by subregion functions assigned to the subregions of the image field. Courses of the plurality of wavefront aberrations over the image field are reproducible with the smooth functions. The influence of incorrect positioning of the spatially resolving sensor on the measurement values of the plurality of wavefront aberrations is reproducible with the subregion functions.

This method facilitates a cost-effective measurement since measurement values are provided in a plurality of subregions of the image field. This may have as a consequence that the measurement values have measurement errors due to incorrect positioning of the sensor. Instead of carrying out a separate error correction, the wavefront aberrations of interest are treated together and approximated simultaneously in the method described above. Use is made of smooth functions assigned to the considered wavefront aberrations, said smooth functions rendering the courses of the wavefront aberrations over the image field reproducible, and subregion functions assigned to the subregions of the image field. The subregion functions are selected in such a way that these reproduce or model actual effects of incorrect positioning of the sensor on the measured wavefront aberrations. In this way, an accurate and reliable correction of the wavefront aberrations is possible and it is therefore possible to provide corrected wavefront aberrations which have good correspondence with the actual wavefront aberrations.

The effects of incorrect positioning of the spatially resolving sensor on the measured wavefront aberrations may be determined, for example, with a measurement or a simulation, e.g. by beam propagation. On the basis hereof, it is possible to set the subregion functions used in the method. By way of example, incorrect positioning in relation to translation degrees of freedom and rotation degrees of freedom may be described with the subregion functions. In relation to an orthogonal xyz-coordinate system, it is possible to model dx-, dy-, dz-translations and drx-, dry-, drz-rotations.

Further possible embodiments and details of the method for common correction of a plurality of wavefront aberrations are described below. In so doing, it is possible to use, to a large part, the same or corresponding features and analogous steps as described above with reference to the method for establishing a single corrected variable. Within this meaning, reference is made to the description above.

By way of example, the wavefront aberrations may be caused by an imaging optical unit of an optical system. Within the scope of the radiation measurement, the spatially resolving sensor may be irradiated by the radiation coming from the imaging optical unit. In this context, reference is further made to the possibility of carrying out the method for establishing the plurality of corrected wavefront aberrations and of adjusting the imaging optical unit on the basis thereof.

By way of example, the wavefront aberrations corrected with the method may be available in the form of coefficients for Zernike polynomials of a wavefront expansion. By way of example, using the method, it is possible to correct the Zernike coefficients for the Zernike polynomials Z2, Z3 and Z4 together.

In a further embodiment, the spatially resolving sensor is arranged at different measurement positions. Here, measurement errors may be caused by incorrect positioning of the sensor.

It is also possible for the spatially resolving sensor to have a plurality of partial sensors. Here, incorrect positioning and measurement errors as a result thereof may be a consequence of position errors of partial sensors of the sensor.

The employed smooth functions may each comprise a plurality of basis functions. By way of example, the smooth functions may be polynomial functions.

In a further embodiment, the correction comprises forming corrected values of the plurality of wavefront aberrations. Here, error-afflicted measurement values of the wavefront aberrations may be replaced by the corresponding corrected values, which may also be referred to as reconstructed values.

In a further embodiment, the approximation comprises determining coefficients of the subregion functions. Moreover, measurement values of the plurality of wavefront aberrations are corrected using the coefficients of the subregion functions. In this way, it is possible to form corrected values for replacing error-afflicted measurement values of the wavefront aberrations.

Aforementioned method variants, in which components such as e.g. a function matrix or the pseudoinverse thereof are used, may be used in an analogous fashion. Possible embodiments are described in more detail below.

In a further embodiment, the approximation comprises forming a function matrix from subregion functions and basis functions of the smooth functions, forming the pseudoinverse of the function matrix, and multiplying the pseudoinverse of the function matrix by a vector of measurement values of the plurality of wavefront aberrations to form a coefficient vector. The coefficient vector comprises coefficients of the subregion functions and coefficients of the basis functions of the smooth functions. In this way, it is possible to meet the demand for an approximation to the measurement values of the wavefront aberrations by the smooth functions and the subregion functions with minimal deviation, and reliably provide coefficients of the subregion functions.

In a further embodiment, the correction comprises multiplying a matrix of subregion functions by a vector of coefficients of the subregion functions (established through the approximation) to form a product and subtracting the product, apart from the mean value thereof, from the vector of measurement values of the plurality of wavefront aberrations. In this way, it is possible to form corrected values of the wavefront aberrations which may substantially correspond to the actual wavefront aberrations.

The product may relate to the entries or weightings of all approximated subregion functions. The phrase "apart from the mean value thereof" may be satisfied by virtue of the mean value of the product being subtracted from the product and this term being subtracted from the vector of measurement values of the plurality of wavefront aberrations. What this renders it possible to achieve is that predominantly relative differences in the measurement values of the wavefront aberrations, i.e. differences present from subregion to subregion of the image field and based on measurement errors, are corrected. A uniform or global correction over all subregions of the image field is therefore avoided.

In a further embodiment, subregion functions with a zero mean value are used. These are subregion functions which, in relation to the image field, have a mean value of zero. Such subregion functions may be formed by virtue of the respectively associated mean value being subtracted from each subregion function with a mean value. The use of subregion functions with a zero mean value facilitates a unique approximation and allows the above-described subtraction of the mean value of the product to be implicitly contained in the approximation and correction. Here, the product has a mean value of zero, as a result of which it is possible to dispense with the subtraction. Thus, in relation to the above-described correction step, it is possible to merely subtract the product from the vector of measurement values of the plurality of wavefront aberrations, provided that subregion functions with a zero mean value are used.

Moreover, the following further embodiments, which facilitate a unique approximation, are conceivable. By way of example, if the effects of incorrect positioning of a sensor in respect of a specific degree of freedom are intended to be reproduced by all or some of the subregion functions, with the extent of the incorrect positioning being selected to be the same size for each subregion function for reasons of simplicity, then it is possible to provide modified subregion functions, the sum of which equals zero, for these subregion functions. This is possible by virtue of the scaled sum of all of these subregion functions being subtracted from each one of these subregion functions, with the scaling factor being the reciprocal of the number of these subregion functions. What this may achieve is that these subregion functions only detect differences in the positioning of the sensor in respect of this degree of freedom, but no global incorrect positioning. As an alternative to modifying the subregion functions, this may be achieved by virtue of the associated coefficients being modified accordingly prior to forming the above-described product (product of the matrix of subregion functions with the vector of the coefficients of the subregion functions) provided for subtraction from the vector of measurement values of the plurality of wavefront aberrations.

In a further embodiment, the approximation and correction are carried out together, by virtue of a function matrix being formed from subregion functions and basis functions of the smooth functions, the pseudoinverse of the function matrix being formed, a partial matrix being formed from the pseudoinverse of the function matrix, with coefficients of the subregion functions being generable by way of the partial matrix, a matrix of subregion functions being multiplied by the partial matrix to form a product, the product being subtracted from an identity matrix to form a correction matrix, and the correction matrix being multiplied by a vector of measurement values of the plurality of wavefront aberrations. This embodiment, in which corrected values of the plurality of wavefront aberrations may be formed in a simple manner, likewise meets the demand for obtaining an approximation to the measurement values of the wavefront aberrations by the smooth functions and the subregion functions with minimum deviation.

In addition, or as an alternative, to forming corrected values of the wavefront aberrations, it is possible to carry out a further embodiment in which the correction comprises forming approximated courses of the plurality of wavefront aberrations. This facilitates an elimination of spot noise. Replacing the measurement values of the plurality of wavefront aberrations by the approximated courses may be considered.

Furthermore, an interpolation and/or extrapolation may be carried out by virtue of at least one complementary value of at least one of the wavefront aberrations being formed, with the complementary value belonging to spatial coordinates for which no measurement value of the wavefront aberration is present. This embodiment may be carried out on the basis of an approximated course of the relevant wavefront aberration.

Forming approximated courses of the plurality of wavefront aberrations may be implemented with the following embodiment. Here, a function matrix is formed from subregion functions and basis functions of the smooth functions, the pseudoinverse of the function matrix is formed, a partial matrix is formed from the pseudoinverse of the function matrix, with coefficients of the basis functions of the smooth functions being generable by way of the partial matrix, a matrix of basis functions of the smooth functions is multiplied by the partial matrix to form a course generation matrix, and the course generation matrix is multiplied by a vector of measurement values of the plurality of wavefront aberrations. This embodiment, according to which approximated courses of the plurality of wavefront aberrations may be formed in a simple manner, likewise meets the demand for realizing an approximation to the measurement values of the wavefront aberrations with minimum deviation.

In respect of the above-described method, it is conceivable for the radiation measurement to relate to a plurality of separate, non-overlapping subregions and, additionally, at least one further subregion of the image field which overlaps with at least one of the separate, non-overlapping subregions. Here, at least one subregion of the disjointed subregions, considered in the method, may be considered to be a unified subregion, for which common measurement values of the plurality of wavefront aberrations are provided and for which an assigned subregion function is used for reproducing the influence of incorrect sensor positioning. Such a unified subregion may be composed of overlapping subregions. Common measurement values of the plurality of wavefront aberrations of the unified subregion may be provided on the basis of suitable preprocessing (e.g. stitching) of measurement values initially obtained in the individual overlapping subregions. Subsequently, the unified subregion and the associated measurement values may be used in the common correction or approximation carried out with the smooth functions and the subregion functions. It is also possible to form, and take into account, a plurality of unified subregions.

Instead of working with unified subregions, the following embodiment is possible. Here, measurement values of the plurality of wavefront aberrations are provided in at least one further subregion of the parameter range, with the further subregion overlapping with at least one of the separate and non-overlapping subregions, and the approximation is carried out with a further subregion function, assigned to the further subregion, with which incorrect positioning of the spatially resolving sensor is reproducible. In the case of a plurality of further subregions, a plurality of associated subregion functions are used in a corresponding manner.

Furthermore, use may be made of a corresponding apparatus for establishing a plurality of corrected wavefront aberrations depending on two spatial coordinates, in an image field. The apparatus comprises a spatially resolving sensor for carrying out a radiation measurement, with which it is possible to provide measurement values of the plurality of wavefront aberrations in a plurality of separate and non-overlapping subregions of the image field. The apparatus furthermore comprises an evaluation device for correcting measurement values of the plurality of wavefront aberrations together. The evaluation device is embodied to carry out the correction using an approximation, in which measurement values of the wavefront aberrations are approximated by a plurality of smooth functions assigned to the wavefront aberrations and by subregion functions assigned to the subregions of the image field. Courses of the plurality of wavefront aberrations over the image field are reproducible with the smooth functions. The influence of incorrect positioning of the spatially resolving sensor on the measurement values of the plurality of wavefront aberrations is reproducible with the subregion functions.

Aspects and details described above with reference to the method for common correction of a plurality of wavefront aberrations may also be used in the apparatus.

The advantageous embodiments and developments of the invention, explained above and/or reproduced in the dependent claims, may be used individually—except for e.g. in the case of clear dependencies or incompatible alternatives—or else in any combination with one another.

BRIEF DESCRIPTION OF THE DRAWINGS

The invention is explained in more detail below on the basis of the schematic figures. In detail.

DETAILED DESCRIPTION

A concept for establishing a corrected variable which depends on at least one parameter, in a parameter range of the at least one parameter is described below. Here, measurement values of the variable in a plurality of, or disjoint, i.e. mutually separate and non-overlapping, subregions of the parameter range are provided on the basis of a measurement. This may lead to the measurement values of the variable to be afflicted with measurement errors in individual subregions of the parameter range, said measurement errors occurring individually in the subregions. There may be a variation of the measurement errors from subregion to subregion. Such a falsification of the measurement values of the variable reduces the significance thereof. Such error contributions may be rectified or at least reduced in part or substantially, using the method described here.

For more clarity, the correction method is described in an exemplary manner in conjunction with optical systems 100, 101, which comprise an imaging optical unit 130. The variable to be corrected is a spatially dependent optical variable, to be precise an imaging or wavefront aberration caused by the imaging optical unit 130. This is explained in part on the basis of coefficients for a Zernike polynomial of a wavefront expansion. Zernike coefficients for the Zernike polynomials Z2 and Z3, by which an image aberration in the form of a lateral distortion or image offset are reproduced, and a Zernike coefficient for the Zernike polynomial Z4, reproducing a focal offset, are considered. Here, these are Zernike polynomials according to Noll's indices. In order to simplify the following description, Z2, Z3, Z4 also denote the coefficients for the corresponding Zernike polynomials below.

The associated parameter range of the wavefront aberrations comprises two lateral orthogonal spatial coordinates, denoted by x and y below, and represents a two-dimensional image field 150. In order to simplify the following description, such spatial coordinates x, y, relating to the image field 150, optionally complemented by a further vertical orthogonal spatial coordinate z, are indicated in the figures on the basis of axes of an orthogonal xy- or xyz-coordinate system.

Figure 1:
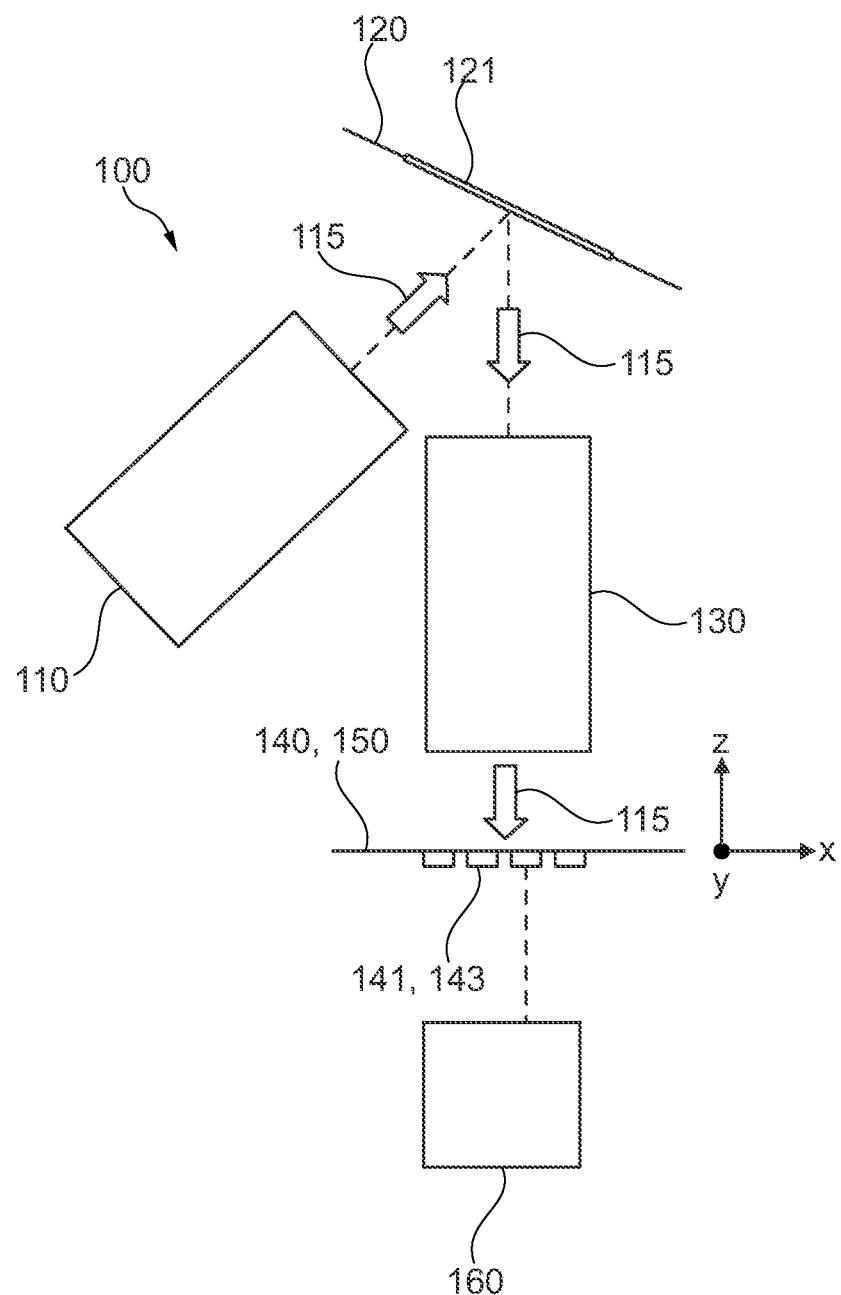
FIG. 1 shows an optical system comprising an imaging optical unit, with which radiation reflected at an object is able to be guided to a sensor.

FIG. 1 shows an optical system 100, which may be used to inspect a reflecting object 121. The object 121 could be a lithography mask or reticle, which may be examined by the inspection system 100 in view of defects. The object 121 is situated in an object plane 120.

The system 100 is configured to irradiate the object 121 with radiation 115. Such elements are combined in FIG. 1 in the form of an illumination system 110. A projection or imaging optical unit 130, which serves to guide a portion of the radiation 115 reflected at the object 121 in the direction of an image plane 140, is a further component of the system 100. In this way, an object field of the object plane 120 may be imaged into an image field 150 of the image plane 140 with the imaging optical unit 130. By way of example, the image field 150 may have lateral dimensions in the two-digit centimeter range, e.g. approximately 21 cm×28 cm.

A spatially resolving sensor 141 embodied for radiation measurement is arranged in the region of the image plane 140, said sensor being able to be irradiated with the radiation coming from the imaging optical unit 130. It is possible for the sensor 141 to be an electronic sensor with an arrangement of radiation-sensitive sensor elements or pixels. In one possible configuration, the sensor 141 is realized in the form of a CCD (charge-coupled device) sensor with radiation-sensitive photodiodes. By way of example, the sensor 141 may be embodied as a time delay and integration charge-coupled device (TDI-CCD) sensor. Use is made of an evaluation device 160, coupled to the sensor 141, for further processing or evaluation of measurement signals from the sensor 141. It is possible to provide measurement values of an optical variable of interest at image points of the image field 150 with the evaluation device 160.

During a mask inspection carried out with the system 100, it is possible, for example, to use radiation 115 with the same wavelength as is also used in a lithography process. Therefore, this process may be referred to as an actinic examination.

Figure 3:
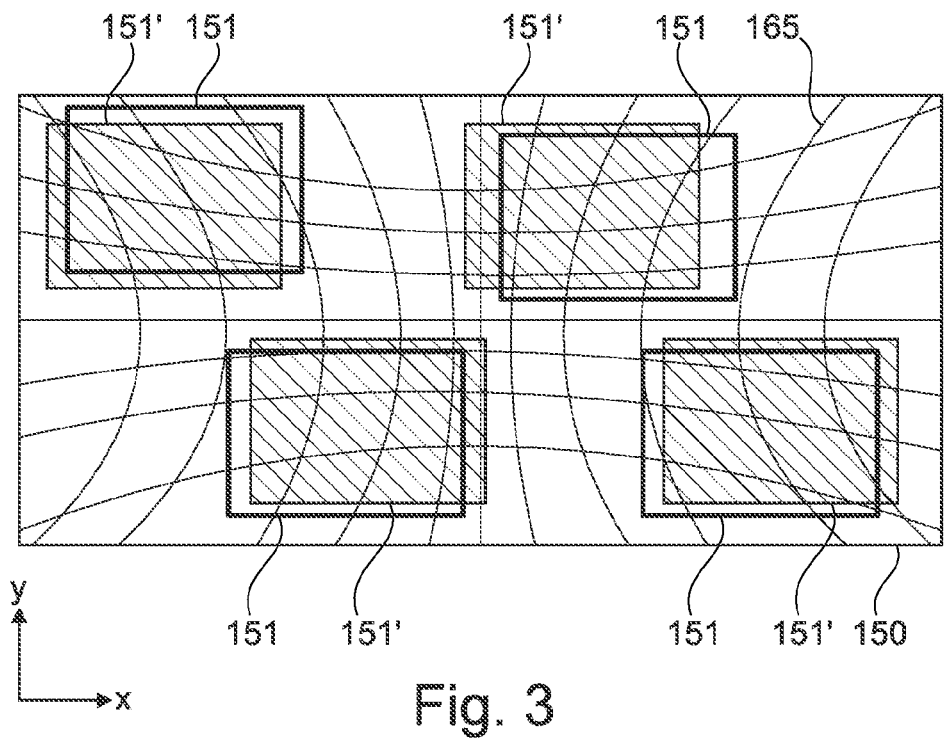
FIG. 3 shows an illustration of an image field with a distortion lattice and with subregions which depict intended measurement positions and actual measurement positions of a sensor deviating therefrom.

In the system 100, radiation is not detected in the whole image field 150 of the imaging optical unit 130, but instead in disjoint subregions 151 of the image field 150 (cf. FIG. 3). Therefore, the sensor 141 does not have an all-over detection region covering the whole image field 150; instead, one configuration has a plurality of spaced-apart spatially resolving partial sensors. Each partial sensor has a corresponding partial arrangement of sensor elements or photodiodes, and hence a corresponding partial detection region. This allows a cost-effective design of the sensor 141 and, as a consequence thereof, a cost-effective measurement. In order to be able to examine a contiguous region of the object or reticle 121 despite the subdivided sensor design, the object 121 may be correspondingly positioned or moved in the object plane 120 within the scope of the examination.

By way of example, each partial sensor of the sensor 141 may comprise a megapixel CCD chip with a number of sensor elements in the region of $10^6$. One example is an arrangement with approximately 3000×3000 pixels.

FIG. 1 indicates an exemplary design of the sensor 141 with four partial sensors, wherein the partial sensors may be arranged in accordance with the subregions 151 in FIG. 3. It is possible for the sensor 141 to have a different or larger number of partial sensors such that a corresponding number of detectable partial fields 151 may also be present.

In respect of the system 100, it is of interest to establish imaging or wavefront aberrations, which may be caused by the imaging optical unit 130. For the wavefront measurement, use may be made of a combination of distortion- and phase-retrieval metrology. The established imaging aberrations may be used to develop adjustment processes for adjusting the imaging optical unit 130 such that the imaging aberrations may be minimized in view of a reliable and accurate functionality of the system 100.

Such establishment of imaging aberrations for the purposes of adjusting the imaging optical unit 130 may already be provided within the scope of the design of the system 100. For this purpose, a single spatially resolving sensor 143 for radiation detection may be used instead of the sensor 141 with partial sensors, as used in the constructed system 100. In order to reproduce a measurement carried out by the sensor 141, the positions of the partial sensors of the sensor 141 may be driven with the sensor 143 and a partial measurement of the radiation 115 may be carried out in each case at these measurement positions. In this way, radiation detection may again take place only in disjoint subregions 151 of the image field 150. The exemplary illustration of FIG. 1 (and correspondingly FIG. 3) may therefore also be considered to be an illustration of four measurement positions of the sensor 143, wherein, in accordance with the description above, a different or larger number of measurement positions may also be considered. It is optionally possible for the sensor 143 to have a detection region with different or larger lateral dimensions than the partial sensors of the sensor 141, and so, accordingly, different or larger subregions 151 of the image field 150 are detectable.

An evaluation device 160 coupled to the sensor 143 is used for further processing or evaluation of measurement signals of the sensor 143. This evaluation device 160 may be different from the evaluation device 160 which is used in the constructed system 100 and assigned to the sensor 141. This may equally apply to the illumination system 110 and the object or reticle 121. In this context, it is furthermore possible, in the case of a measurement with the sensor 143, to use radiation 115 with a different wavelength than in the case of a measurement with the sensor 141.

In a manner comparable with the sensor 141, the sensor 143 may be realized in the form of an electronic sensor, for example in the form of a CCD or TDI-CCD sensor, with an arrangement of radiation-sensitive sensor elements or photodiodes. The sensor may correspondingly have a megapixel CCD chip. After an appropriate evaluation of measurement signals of the sensor 143 with the associated evaluation device 160, measurement values of one or more wavefront aberrations of interest at image points in disjoint subregions 151 of the image field 150 may be provided on the basis of a measurement carried out at different measurement positions of the sensor 143. By way of example, this may relate to the Zernike coefficients Z2, Z3 and/or Z4. By way of example, in view of the coefficients Z2, Z3, the sensor 143 could be a distortion measuring head.

Reference is made to the fact that, within the scope of a measurement of imaging aberrations, use may furthermore be made of an object or reticle 121 with suitable test structures (not depicted here), which may be imaged into the image field 150 by the imaging optical unit 130. It is possible to provide the desired measurement values of the wavefront aberration or aberrations of interest by evaluating associated measurement signals.

By way of example, a grid of marks may be used in relation to detecting a distortion aberration. A distortion of the imaging optical unit 130 causes a displacement of the marks imaged into the image field 150. It is possible to establish the distortion from the position of the imaged marks relative to the intended positions thereof.

Arranging or positioning the sensor 143 at different measurement positions may be carried out with a suitable positioning device, for example with a positioning stage (not depicted here). Here, the positioning accuracy of the sensor 143 is limited by the accuracy of the positioning device. Expressed differently, the measurement may be impaired due to incorrect positioning of the sensor 143. This may relate, in particular, to incorrect positioning in the translation degrees of freedom, i.e. in the x-, y- and z-direction. This leads to the possibility of the provided measurement values of an imaging or wavefront aberration having a constant measurement error or offset in individual subregions 151 of the image field 150. The instances of incorrect positioning may differ, and so the offset errors occurring individually in subregions 151 of the image field 150 may likewise vary and differ from one another in respect of the absolute value and/or sign.

Figure 2:
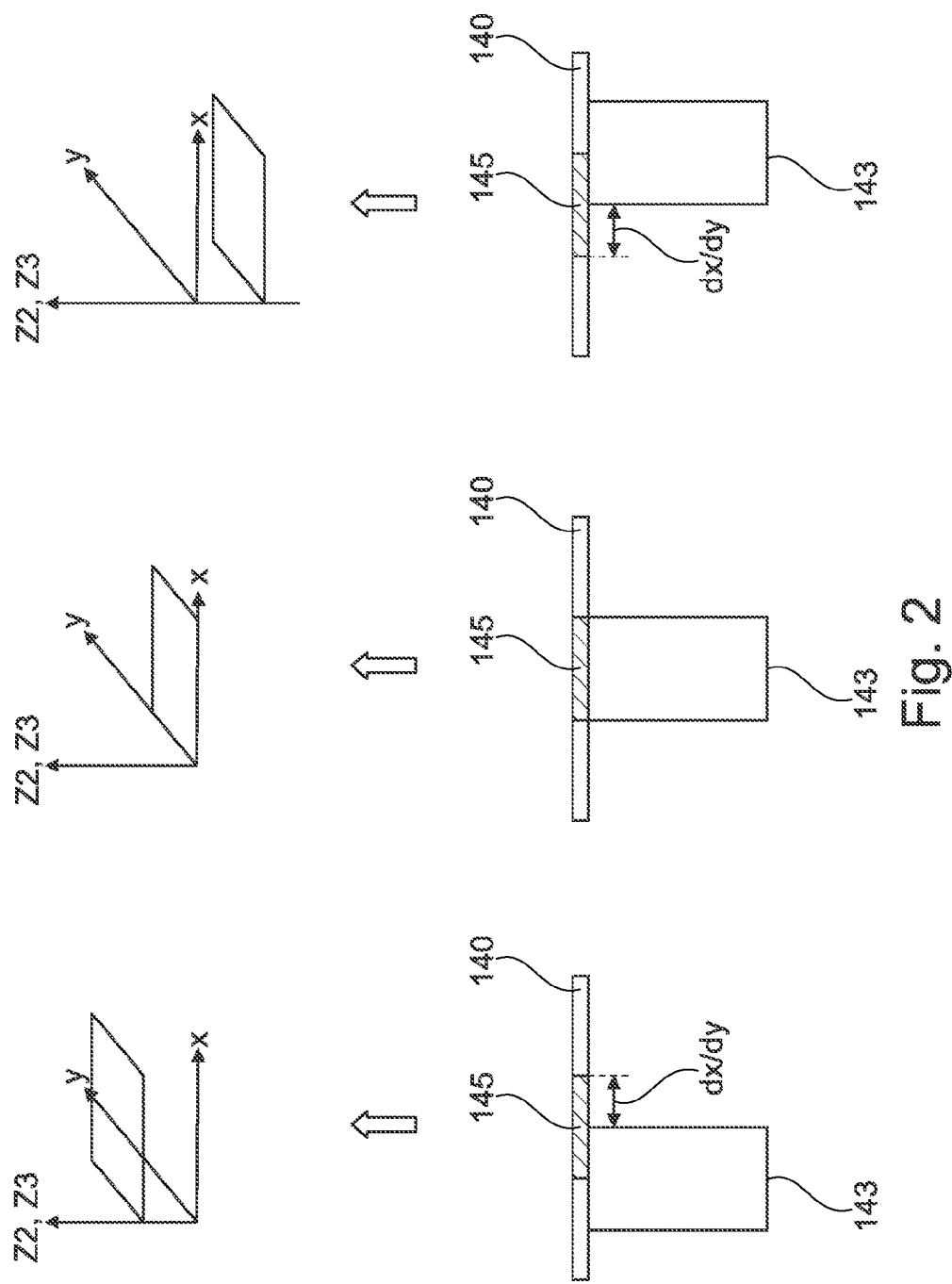
FIG. 2 shows an illustration of measurement positions of a sensor, including lateral incorrect positioning, and the effect thereof on a measurement of a wavefront aberration.

In order to describe this relationship, FIG. 2 shows different lateral measurement positions of the sensor 143 in relation to the image or image sensor plane 140 and the effect thereof on the provision of measurement values of the wavefront aberrations Z2, Z3 reproducing a distortion. Moreover, an intended measurement position 145 provided for the sensor 143 or the detection region thereof is indicated in the image plane 140. Provided the sensor 143 is situated at the intended position 145 thereof, as shown in the middle illustration of FIG. 2, this does not lead to any deviation when measuring the wavefront aberrations Z2, Z3. A consequence of incorrect lateral positioning in the form of a deviation dx or dy of the sensor 143 in relation to the intended measurement position 145, as depicted in the left-hand and right-hand illustration of FIG. 2, is that a deviation in the form of an offset error respectively occurs when measuring the wavefront aberrations Z2, Z3.

Figure 4:
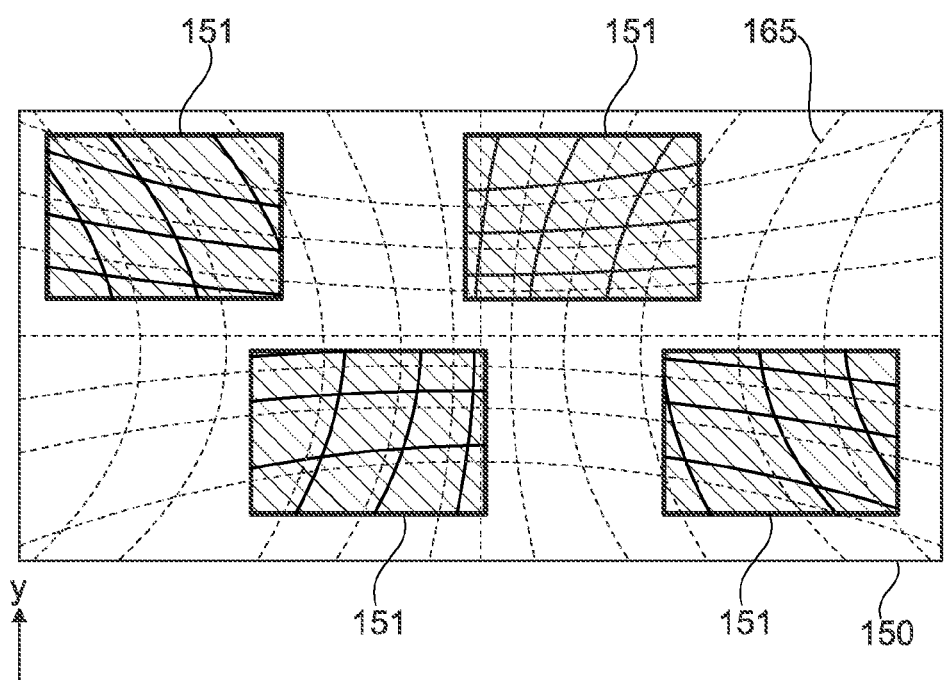
FIG. 4 shows a further illustration of the image field of FIG. 3, with the subregions of the image field belonging to the actual measurement positions being arranged at the intended measurement positions.

FIGS. 3 and 4 describe, in a further illustration, the relationship between lateral positioning errors of the sensor 143 and the measurement of falsifying offset errors. What is shown here are an image field 150 and an exemplary imaging aberration in the form of a pincushion-shaped distortion 165, which is indicated on the basis of a lattice, present in the image field 150. Furthermore, four subregions 151 of the image field 150 are depicted, a radiation measurement being carried out in said subregions with the sensor 143 arranged at different measurement positions.

FIG. 3 shows both the actual measurement positions of the sensor 143 present at the measurement, with the associated detected subregions 151, and the intended measurement positions of the sensor 143, with the associated subregions 151' (indicated by hatching). As a consequence of the different instances of incorrect lateral positioning of the sensor 143, the subregions 151 each have a corresponding offset in relation to the subregions 151'. Therefore, a consequence thereof is that different offset errors occur when measuring the distortion 165, expressed by the Zernike coefficients Z2 and Z3.

This is shown in FIG. 4 by virtue of the subregions 151 of FIG. 3, including the full lattice lines of the distortion 165, being displaced in relation to the intended measurement positions of the sensor 143. Here, the distortion 165 present in the image field 150 is indicated on the basis of dashed lattice lines. The distortions between the full lattice lines and the dashed lattice lines, identifiable in the subregions 151 in FIG. 4, make the offset errors occurring during the measurement clear.

Figure 5:
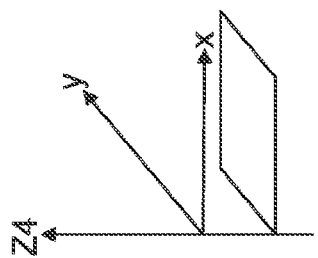
FIG. 5 shows a further illustration of measurement positions of a sensor, including vertical incorrect positioning, and the effect thereof on a measurement of a wavefront aberration.
Figure 5:
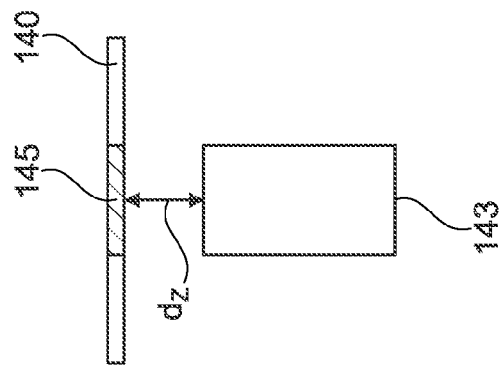
Figure 5:
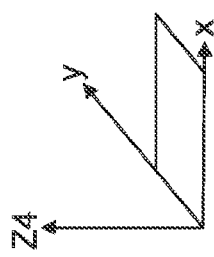
Figure 5:
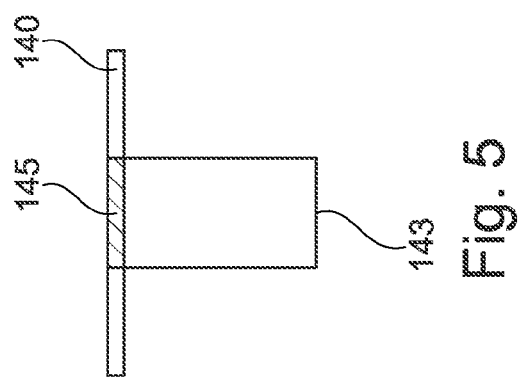
Figure 5:
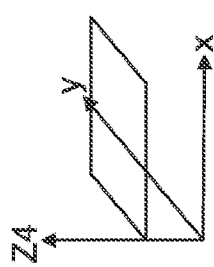
Figure 5:
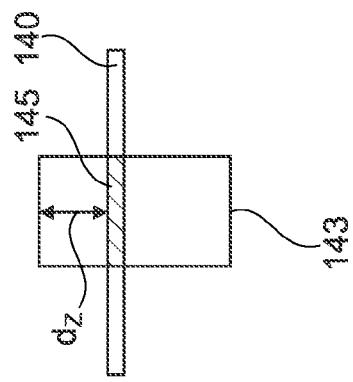

When measuring the wavefront aberration Z4, which reproduces a focal offset, the vertical incorrect positioning of the sensor 143 may lead to the occurrence of offset errors. In order to depict this relationship, FIG. 5 shows different vertical measurement positions of the sensor 143 in relation to the image sensor plane 140 and the effect thereof on the provision of measurement values of the wavefront aberration Z4. Provided the sensor 143 or the detection region thereof is situated at the intended measurement position 145 thereof, as indicated in the middle illustration of FIG. 5, this does not lead to any deviation when measuring the wavefront aberration Z4. Incorrect positioning in relation to the height in the form of a vertical deviation dz, as shown in the left-hand and right-hand illustration of FIG. 5, in each case has as a consequence an occurrence of an offset error when measuring the wavefront aberration Z4.

Incorrect positioning dx, dy, dz of the sensor 143 is expressed in the disjointedly measured wavefront aberrations by way of offset errors, i.e. apparent image aberrations. Within the subregions 151, detected by the sensor 143, of the image field 150, the offset errors are constant or substantially constant, and thus cause an offset of the measured wavefront aberrations, including the mean values of the wavefront aberrations, in the corresponding subregions 151. A variation of the offset errors may be present from subregion 151 to subregion 151 and, as non-systematic measuring errors, from measurement to measurement as well. The offset errors could be significantly greater than other measurement errors and, in particular, greater than the field variation of the actual or true wavefront aberrations. This may apply, in particular, to the wavefront aberrations or low-order Zernike coefficients, in particular Z2, Z3 and Z4. This renders the determination of suitable adjustment processes more difficult and may lead to the system 100 ultimately not meeting the specification.

The provision of measurement values of one or more imaging aberrations of interest, e.g. of the wavefront aberrations Z2, Z3 and/or Z4, at image points in disjoint subregions 151 of the image field 150 may be considered in a comparable manner with respect to the system 100 which is equipped with the sensor 141 with a plurality of non-overlapping partial sensors. To this end, a measurement is carried out with the sensor 141 and measurement signals of the sensor 141 are evaluated with the associated evaluation device 160 for the purposes of providing the measurement values. A further adjustment or fine adjustment of the imaging optical unit 130 may be undertaken on the basis thereof.

It is possible that the arrangement of the partial sensors of the sensor 141 is afflicted with errors such that the partial sensors have position errors, in particular in relation to the degrees of freedom x, y, z. In a manner comparable to the positioning errors of the sensor 143 described above, such position errors may lead to an occurrence of constant or substantially constant offset errors in the subregions 151 of the image field 150 when measuring the wavefront aberrations Z2, Z3, Z4 (possibly also crosstalk to higher order imaging aberrations). Reference is made to the description above in respect of further details in relation thereto.

The position errors of the image sensors of the sensor 141 may be a consequence of installation errors, but may also be caused during the operation and/or throughout the service life by way of drifts, such as e.g. temperature-induced changes in the size of components. Therefore, both systematic measurement errors, i.e. errors which are the same in each measurement, and non-systematic measurement errors, i.e. errors which differ from measurement to measurement, may be present. This also leads to an impairment of the adjustment of the imaging optical unit 130.

The highlighted problem in the case of the system 100 operating on the basis of reflection may also occur in a transmission-operated inspection system, in which a transmitted radiation component is detected. Such a system 101, which substantially has the same design and the same functionality as the system 100, is shown schematically in FIG. 6. Reference is made to the fact that corresponding aspects and components which are the same or have the same effect are not described again in detail here but that, instead, reference is made to the description above.

The optical system 101 likewise comprises an illumination system 110 for illuminating an object 122 arranged in an object plane 120 with radiation 115. The object 122, which may be partly transilluminated, may be a reticle. A component of the radiation 115 transmitted through the object 122 is guided in the direction of an image plane 140 with an imaging optical unit 130. An object field of the object plane 120 may be imaged into an image field 150 of the image plane 140 by way of the imaging optical unit 130. A spatially resolving sensor 141 with a plurality of partial sensors, the measurement signals of which may be processed further or evaluated by way of an evaluation device 160, is arranged in the region of the image plane 140. In this way, radiation is detected in disjoint subregions 151 of the image field 150 (cf. FIG. 3).

In relation to the system 101, it is likewise of interest to establish imaging or wavefront aberrations with a measurement in order to be able to adjust the imaging optical unit 130 on the basis thereof. To this end, a single spatially resolving sensor 143, which is moved to the positions of the partial sensors of the sensor 141 for radiation detection purposes, may be used within the scope of the design of the system 101 in place of the sensor 141. Incorrect positioning of the sensor 143 in the translation degrees of freedom x, y, z then may lead to the provided measurement values of wavefront aberrations of interest, e.g. Z2, Z3 and/or Z4, being afflicted with offset errors. Such offset errors may occur individually in the subregions 151 of the image field 150 and may differ from offset errors in other subregions 151. This is likewise the case when carrying out a measurement with the sensor 141 in the set up system 101, wherein the offset errors in this case may be caused by position errors of the partial sensors of the sensor 141. In respect of further details, reference is made to the explanations above. This also relates to the aspect of using an object or reticle 122 with suitable test structures (not depicted here) when measuring imaging aberrations.

Possible configurations of a method for correcting error-afflicted measurement values of an imaging aberration of interest, which may be provided—as explained above—on the basis of a measurement with the sensor 141 of the system 100 or 101 or the sensor 143 at image points in disjoint subregions 151 of an image field 150, are described below. A reliable adjustment of the associated imaging optical unit 130 may be undertaken on the basis thereof. Individual ones of the explained steps for suppressing the measurement errors may be carried out by, or with, the evaluation device 160 connected to the sensor 141 or 143. The sensor 141 or 143 and the associated evaluation device 160 may, within this meaning, form an apparatus for establishing a corrected imaging aberration.

With respect to the system 100 or 101 provided with the sensor 141, it may be expedient to carry out the suppression for each measurement. This may be considered in the case of predominantly non-systematic measurement errors. In the case of predominantly systematic measurement errors, the correction may be provided in the form of a permanent calibration on the basis of one or more measurements, for example once or at regular intervals.

What is exploited for suppressing the offset errors occurring in the subregions 151 of the image field 150 is that an actual imaging aberration, i.e. an imaging aberration not afflicted by measurement errors, may have regularities or predictable properties in relation to the overall image field 150 and may be described by a smooth function over the image field 150. This does not, or substantially not, apply to the offset errors which occur individually in the subregions 151 of the image field. In order to take these circumstances into account, the correction is carried out with the application of an approximation in which provided measurement values of the imaging aberration of interest are approximated by a smooth function and by subregion functions assigned to the subregions 151 of the image field 150.

A course of the imaging aberration over the image field 150 is reproducible with the smooth function. The employed smooth function or the basis functions thereof may be set with knowledge of the functionality of the imaging optical unit 130. The subregion functions are selected in such a way that, within the scope of the approximation, the considered imaging aberration may be changed by the same value in each case in the individual subregions 151 of the image field 150. In this manner, it is possible to reproduce the effect of an error-afflicted measurement or the individual occurrence of the offset error falsifying the actual imaging aberration in the subregions 151 of the image field 150. As a result, an accurate approximation to the measurement values with a minimum deviation may be obtained, which in turn allows reliable resetting or suppression of the measurement errors.

Before possible configurations of the correction procedure are described in detail, the following boundary conditions and definitions are initially set.

The object or image field 150 is described at N discrete field points $(x_i, y_i)$. Here, $x_i$ and $y_i$ are the corresponding spatial coordinates of the image points and $i=1, 2, \ldots, N$ applies.

The coordinates $x_i$ and $y_i$ of all image points of the image field 150 are preferably selected in such a way that the mean value of all coordinates $x_i$ and the mean value of all coordinates $y_i$ is zero in each case. Setting the coordinate origin thus was found to be expedient from a numerical point of view.

The image field 150 comprises n subregions 151, which are also denoted by $F_l$ below. Here, $l=1, 2, \ldots, n$ applies. Moreover, $n_l$ of the N image points $(x_i, y_i)$ belong to the subregion $F_l$. Moreover, $$\sum_{l=1}^{n} n_l = N, \tag{1}$$

applies, i.e. each image point belongs to exactly one subfield $F_l$.

The following notation is introduced for variables which depend on the image points:

$$f_i = f(x_i, y_i), \text{ for } i=1,2,\ldots,N \tag{2}$$

$f_i$ is therefore the value of a spatially dependent function. Furthermore, use is made of the following definition:

$$\vec{f} := \begin{pmatrix} f_1 \\ f_2 \\ \vdots \\ f_N \end{pmatrix} \tag{3}$$

An example thereof is the collection of all spatial coordinates of the image points in accordance with:

$$\vec{x} := \begin{pmatrix} x_1 \\ x_2 \\ \vdots \\ x_N \end{pmatrix}, \vec{y} := \begin{pmatrix} y_1 \\ y_2 \\ \vdots \\ y_N \end{pmatrix} \quad (4)$$

Moreover, the following terms or vectors are introduced, i.e. the mean value in accordance with $$<f> := \frac{1}{N} \sum_{i=1}^{N} f_i \quad (5)$$

and the norm $$\|\vec{f}\| := \sqrt{\sum_{i=1}^{N} f_i^2} = \vec{f} \cdot \vec{f} \quad (6)$$

with the canonical scalar product "·".

The component-wise multiplication "⊗" of vectors $\vec{a}$, $\vec{a}$ is defined as follows:

$$\vec{f} \otimes \vec{g} := \begin{pmatrix} f_1 \cdot g_1 \\ f_2 \cdot g_2 \\ \vdots \\ f_N \cdot g_N \end{pmatrix} \quad (7)$$

In formula (7), "·" in each case denotes normal multiplication of numbers.

The component-wise exponentiation is defined as follows:

$$\vec{f}^{(\nu)} := \begin{pmatrix} f_1^\nu \\ f_2^\nu \\ \vdots \\ f_N^\nu \end{pmatrix} \quad (8)$$

By way of example, the following follows therefrom:

$$\vec{f}^{(0)} := \begin{pmatrix} 1 \\ 1 \\ \vdots \\ 1 \end{pmatrix}, \vec{f}^{(1)} = \vec{f}, \vec{f}^{(2)} = \vec{f} \otimes \vec{f}, \vec{f}^{(\nu+1)} = \vec{f}^{(\nu)} \otimes \vec{f}, \text{ etc.} \quad (9)$$

A two-dimensional polynomial function of orders $w_x$ and $w_y$ in x and y, respectively, may be predetermined for the smooth function used in the approximation on account of the dependence of the imaging aberration of interest on two spatial coordinates. The associated basis functions or vectors of orders $\mu$ and $\nu$ in x and y, respectively, may be defined as follows:

$$\vec{p}_{\mu,\nu} = \vec{x}^{(\mu)} \otimes \vec{y}^{(\nu)} = \begin{pmatrix} x_1^\mu \cdot y_1^\nu \\ x_2^\mu \cdot y_2^\nu \\ \vdots \\ x_N^\mu \cdot y_N^\nu \end{pmatrix} \quad (10)$$

Here, $\mu=0, 1, 2, \ldots, w_x$ and $\nu=0, 1, 2, \ldots, w_y$ apply.

The characteristic subregion functions, or the corresponding vectors thereof, used in the approximation, with which the imaging aberration is changeable, in each case by the same value, in the individual subregions $F_l$ of the image field 150 may be set as follows using the identity matrix I:

$$\vec{t}_l(x_i, y_i) := I_{F_l}(x_i, y_i), \quad (11)$$

$$\text{with } \vec{t}_l = \begin{pmatrix} t_{l1} \\ t_{l2} \\ \vdots \\ t_{lN} \end{pmatrix} \text{ and } t_{li} = \begin{cases} 1, (x_i, y_i) \in F_l \\ 0, \text{ else} \end{cases}$$

Here, i=1, 2, ..., N and l=1, 2, ..., n.

Vividly, this means the entries of a subregion function $\vec{t}_l$ which belongs to image points which lie in the associated subregion $F_l$ equal one. By contrast, the entries of $\vec{t}_l$ in relation to the image points of other subregions equal zero.

An actual imaging aberration, e.g. the Z2, Z3 or Z4 coefficient of a wavefront aberration, which is denoted as $$\vec{a} = \begin{pmatrix} a_1 \\ a_2 \\ \vdots \\ a_N \end{pmatrix} = \begin{pmatrix} a(x_1, y_1) \\ a(x_2, y_2) \\ \vdots \\ a(x_N, y_N) \end{pmatrix} \quad (12)$$

below, may be falsified in the measurement by measurement errors. These include the aforementioned (incorrect) offsets, to be remedied, in the subfields $F_l$ of the image field 150, which falsify the actual imaging aberration $\vec{a}$ by a term $$\vec{b} = \sum_{l=1}^{n} \tilde{\alpha}_l \vec{t}_l. \quad (13)$$

The common mean value of the offset errors $$<b> = \sum_{l=1}^{n} \frac{\tilde{\alpha}_l n_l}{N} \quad (14)$$

changes nothing in respect of the form of the course of the imaging aberration over the image field 150 and cannot be determined from the requirement of a smooth course over the field 150. However, a variation from subregion to subregion $F_l$ of the image field 150, caused by the offset errors, may be determined therefrom and corrected thereby.

To this end, the set of functions made of a smooth function and subregion functions is approximated to the measured imaging aberrations or the corresponding measurement values, denoted by the vector $\vec{a}'$ below. To this end, the following procedure may be considered, in which, initially, matrices, i.e. a matrix of the subregion functions $$T := (\vec{t}_1 \ \vec{t}_1 \ \ldots \ \vec{t}_1) \qquad (15)$$

and a matrix of the basis functions of the smooth function $$P := (\vec{p}_{0,0} \ \vec{p}_{0,1} \ \ldots \ \vec{p}_{0,w_y} \vec{p}_{1,0} \vec{p}_{1,1} \ \ldots \ \vec{p}_{w_x,w_y}) \qquad (16),$$

are defined. The aforementioned matrices are combined in the function matrix $$M = (T P) \qquad (17).$$

For the employed functions, such an approximation to the measurement values $\vec{a}\,'$ of the imaging aberration of interest is sought-after that only a minimal deviation still remains. This may be described by the approximation or fitting problem $$\|M \cdot \vec{a} - \vec{a}\,'\|^2 = \text{minimal} \qquad (18),$$

where $$\vec{c} = \begin{pmatrix} \vec{\alpha} \\ \vec{\beta} \end{pmatrix} \qquad (19)$$

is a coefficient vector belonging to the function matrix M. Here, the vector $$\vec{\alpha} = \begin{pmatrix} \alpha_1 \\ \vdots \\ \alpha_n \end{pmatrix} \qquad (20)$$

comprises the coefficients belonging to the subregion functions and the vector $$\vec{\beta} = \begin{pmatrix} \beta_{0,0} \\ \beta_{0,1} \\ \vdots \\ \beta_{w_x,w_y} \end{pmatrix} \qquad (21)$$

comprises the coefficients belonging to the basis functions of the smooth function. It is possible to set or reproduce the weightings of the individual functions by way of the coefficients.

A solution to the fitting problem specified in formula (18) of obtaining an approximation with a minimum deviation to the measurement values by the smooth function and the subregion functions is rendered possible by the following procedure which is able to be carried out with the evaluation device 160. Here, after forming the function matrix M, the pseudoinverse $M^-$ of the function matrix M is formed and multiplied by the vector $\vec{a}\,'$ of measurement values of the imaging aberration in accordance with $$\vec{c} = M^- \cdot \vec{a}\,' \qquad (22)$$

in order to obtain the coefficient vector $\vec{c}$.

The vector $\vec{c}$ contains the weighting coefficients $\vec{\alpha}$ of the subregion functions. These are linked to the offset errors occurring during the measurement and may therefore be used for error suppression, as described below.

The error correction performable with the evaluation device 160 may relate to providing corrected values of the imaging aberration, denoted below by the vector $\vec{a}_{korr}$. Here, the measurement values $\vec{a}\,'$ of the imaging aberration may be replaced by the corrected values $\vec{a}_{korr}$. The corrected values $\vec{a}_{korr}$, which may substantially correspond to the actual imaging aberration $\vec{a}$, may be used when adjusting the imaging optical unit 130.

In order to provide the corrected values $\vec{a}_{korr}$, the vector $\vec{c}$ is formed in accordance with formula (22) in order to obtain the coefficient vector $\vec{\alpha}$ therefrom in accordance with equation (19) and the matrix T of the subregion functions is multiplied by the associated coefficient vector $\vec{\alpha}$ for the purposes of forming a product. The product relates to the entries or weightings of all approximated subregion functions. In order to form the corrected values $\vec{a}_{korr}$, the product, apart from the mean value thereof, is subtracted from the vector $\vec{a}\,'$ of the measurement values as follows:

$$\vec{a}_{korr} = \vec{a} = (T \cdot \vec{\alpha} - \langle T \cdot \vec{\alpha} \rangle) \qquad (23)$$

Here, the mean value of the product may be subtracted from the product and this term may be subtracted from the vector $\vec{a}\,'$. In this way, it is possible to ensure that it is predominantly relative offsets or differences in the measurement values $\vec{a}\,'$, which are caused by the offset error and present from subregion to subregion of the image field 150, which are corrected and that there is substantially no global or uniform variable correction over all subregions. What may be achieved thereby is that the corrected values $\vec{a}_{korr}$ come close to the actual imaging aberration $\vec{a}$, apart from a small difference in the form of a constant or global offset value and spot noise. As a consequence, a reliable reconstruction of the mean values of the measured imaging aberration, which are shifted due to the offset error, is possible in the subregions $F_1$.

Compared to the simpler solution of eliminating the mean values of the imaging aberration of interest, which are initially not measurable as they disappear in the offset errors, in the subregions $F_1$ of the image field 150 by virtue of the associated mean value being in each case subtracted from the measurement values $\vec{a}\,'$ in each one of the subregions $F_1$ or by virtue of not taking into account the mean values of the imaging aberration in the case of an adjustment calculation, the procedure described above is advantageous in that these variables may also be taken into account when adjusting the imaging optical unit 130. However, the application of the simpler solution may be considered in the case where the regularity of the field course of the imaging aberration is disturbed by other measurement error contributions to such an extent that an expedient correction, and hence reconstruction of the mean values of the imaging aberration, is no longer possible in the subregions $F_1$. What this may prevent is that the adjustment of the imaging optical unit 130 is carried out on the basis of measurement errors or measurement noise.

Figure 7:
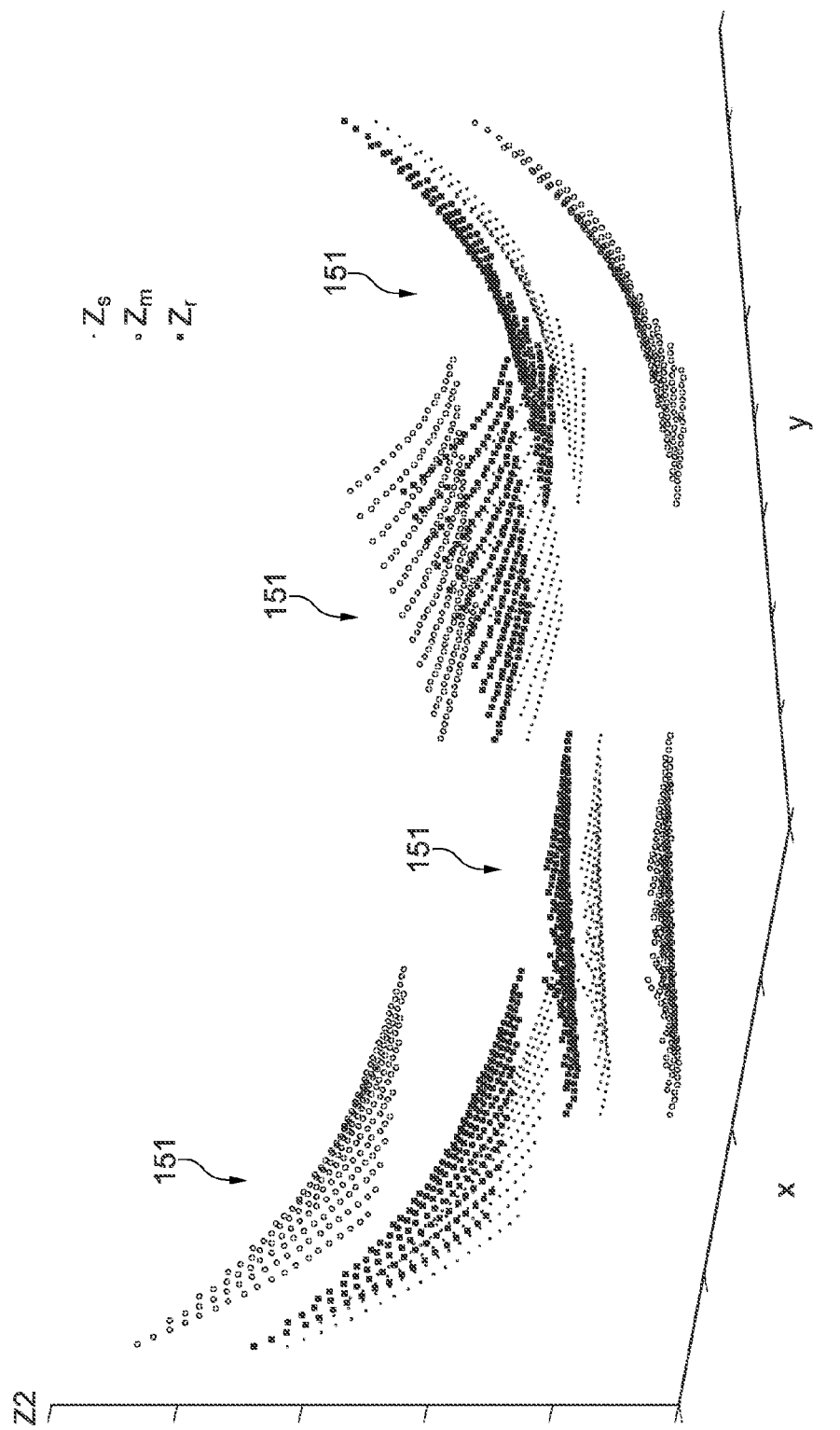
FIG. 7 shows an illustration of values of a wavefront aberration at image points in subregions of an image field, comprising actual, measured and reconstructed values of the wavefront aberration.

For the further elucidation of the method for correcting error-afflicted or noisy measurement values supported by the approximation with a smooth function and subregion functions, FIG. 7 shows exemplary results of a simulation in respect of a wavefront aberration Z2. This relates to the values of the wavefront aberration Z2 at image points in four subregions 151 of an image field 150, wherein the subregions 151 may be arranged in accordance with FIG. 3.

Simulated actual values $Z_s$ of the wavefront aberration Z2 in the subregions 151, present at image points of the image field 150, are described on the basis of relatively small points (true state). The values $Z_s$ were simulated on the basis of rigid body tilts or movements of lens mirrors of an imaging optical unit 130.

Simulated measured values $Z_m$ of the wavefront aberration Z2 at the corresponding image points are indicated by the circular points. Here, this is the sum of the actual values $Z_s$ and offset errors accompanying the measurement, said offset errors being substantially the same in each one of the subregion 151 and differing from subregion 151 to subregion 151 in respect of the sign and/or the magnitude. The difference between the values $Z_s$ and $Z_m$ is approximately constant in each one of the subregions 151 on account of the offset error. Therefore, the functional course of the wavefront aberration Z2 (e.g. the curvature) is almost the same for $Z_s$ and $Z_m$ in each one of the subregions 151.

FIG. 7 moreover shows reconstructed values $Z_r$, formed using the above-explained correction procedure, of the wavefront aberration Z2 at the image points in the subregions 151 on the basis of larger, filled points. The smooth function used here was a third-order polynomial in x and a fifth-order polynomial in y. It is possible to see that the same offset between the corrected values $Z_r$ and the actual values $Z_s$ of the wavefront aberration Z2 is present in each one of the subregions 151. This is the aforementioned small global offset between the values of $Z_r$ and $Z_s$. On the basis of this illustration, it becomes clear that the correction method renders possible a reliable suppression of offset errors, which are a consequence of the measurement in disjoint subfields 151 of the image field 150.

Different developments, which may render an improvement possible, may be considered for the correction method which was explained above and, in accordance with formula (18), based on an approximation with a smooth function and subregion functions. Such configurations of the correction process, which may likewise be able to be carried out with the evaluation device 160 and which may serve as the basis for adjusting the imaging optical unit 130 in the same way, are discussed in more detail below. Below, corresponding features and aspects are not described in detail again. In respect of details thereof, reference is made instead to the description above. Moreover, reference is made of the possibility of applying a plurality of the variants explained below together and/or of combining features of two or more of the described configurations.

In one possible variant, subregion functions $\tilde{t}_i$ with a mean value of zero, which have a mean value of zero in relation to the image field 150, are used in place of the subregion functions $\vec{t}_1$ defined above in accordance with formula (11). Such subregion functions may be formed by virtue of the respectively associated mean value being subtracted from each subregion function $\vec{t}_1$ with a mean value:

$$\tilde{t}_l := \vec{t}_1 - <\vec{t}_1> \quad (24)$$

Carrying out the above-described steps, i.e. forming the function matrix M, forming the pseudoinverse $M^-$, forming the coefficient vector $\vec{a}$, forming the corrected values $\vec{a}_{korr}$ of the considered imaging aberration, with subregion functions with a mean value of zero, offers a number of advantages. By way of example, this includes being able to dispense with the above-explained subtraction of the mean value of the product (weightings of all approximated subregion functions) when forming the corrected values $\vec{a}_{korr}$ of the imaging aberration. This subtraction may be implicitly contained on account of the subregion functions with a zero mean value, and so the mean value of the product may have a value of zero. Therefore, deviating from formula (23), the corrected values may be formed as follows:

$$\vec{a}_{korr} = \vec{a}' - T \cdot \vec{a}, \text{ with } T = (\tilde{t}_l \ \tilde{t}_l \ \ldots \ \tilde{t}_l) \quad (25)$$

Moreover, the approximation may be unique. This is because the mean value of the entries of the subregion functions may, in the case of subregion functions with a mean value, be included twice in the set of used functions, to be precise as a constant in the smooth function and as a sum of the subregion functions in accordance with:

$$\sum_{l=1}^{n} \vec{t}_l = \begin{pmatrix} 1 \\ 1 \\ \vdots \\ 1 \end{pmatrix} \quad (26)$$

As a result, the approximation may be non-unique.

A further numerical improvement may be obtained by the regularization set forth below. In this case, the method, or the steps specified above, is, or are, not carried out with the simple polynomial basis functions in accordance with formula (10), but instead with orthogonalized or with orthonormalized basis functions. In a further variant, use is made of normalized polynomial basis functions. This simplifies an expedient regularization with a singular value threshold which, for example, may be applied when calculating the pseudoinverse M.

Moreover, a simplification of the procedure, which is able to be carried out with the evaluation device 160, to the extent that the approximation and correction are carried out together is possible. To this end, use is made of subregion functions $\tilde{t}_l$ with a zero mean value in accordance with formula (24) and the provided pseudoinverse $M^-$ of the function matrix M is decomposed into two partial matrices, wherein the coefficients $\vec{a}$ of the subregion functions are generable by way of one partial matrix $M_T^-$ and the remaining coefficients $\vec{\beta}$ are generable by way of the other partial matrix $M_P^-$:

$$M^- = \begin{pmatrix} M_T^- \\ M_P^- \end{pmatrix} \quad (27)$$

Using the subregion functions $\tilde{t}_l$ with a zero mean value and the partial matrix $M_T^-$, the relationship between the corrected and measured values of the imaging aberration, described in accordance with formula (25), may be described as follows:

$$\vec{a}_{korr} = \vec{a}' - T \cdot \vec{a} = \vec{a}' - T \cdot M_T^- \cdot \vec{a}' = (I - T \cdot M_T^-) \cdot \vec{a}' = S \cdot \vec{a}', \quad (28)$$

$$\text{with } T = (\tilde{t}_l \ \tilde{t}_l \ \ldots \ \tilde{t}_l) \quad (29)$$

Here, I is the identity matrix. The matrix S, formed by subtracting the product of the matrix T of the subregion functions $\tilde{t}_i$ with a zero mean value and the partial matrix $M_T^-$ from the identity matrix I, i.e.

$$S := I - T \cdot M_T^- \quad (30)$$

is referred to as correction matrix below.

By providing or forming the correction matrix S in accordance with formula (30), it is possible to carry out the procedure of correcting the offset error for forming corrected values of the imaging aberration of interest with a simple multiplication of the measurement values by the matrix S:

$$\vec{a}_{korr} = S \cdot \vec{a} \quad (31)$$

Forming the matrix S and the multiplication likewise leads to a solution of the fitting problem specified in formula (18) of obtaining an approximation to the measurement values by the smooth function and the subregion functions with minimal deviation.

In this context, reference is furthermore made to the option of using the correction matrix S, formed once, to correct measurement values of the imaging aberration, which are obtained with various measurements, in each case.

A further variant of the error correction which is able to be carried out with the evaluation device 160 consists of forming an approximated course of the imaging aberration in addition, or as an alternative, to corrected aberration-remedied values of the considered imaging aberration. The approximated course may substantially correspond to the actual imaging aberration, i.e. the imaging aberration without a measurement error. In this case, it is also possible to replace error-afflicted measurement values of the imaging aberration by the approximated course and to undertake an adjustment of the imaging optical unit 130 on the basis of the approximated course.

Spot noise may be eliminated by forming the approximated course of the imaging aberration. However, it is possible that, in contrast to the corrected values of the imaging aberration, local image aberrations are no longer contained in the approximated course and, as a result thereof, may possibly no longer be identifiable. This disadvantage may be circumvented by virtue of also forming corrected values of the imaging aberration, or taking these into account during the adjustment, in addition to the approximated course.

The approximated course may likewise be formed within the scope of an approximation and correction carried out together. To this end, a procedure comparable to the above-described simplification may be carried out, wherein subregion functions $\tilde{t}_i$ with a zero mean value in accordance with formula (24) are used and the pseudoinverse $M^-$ of the function matrix M is decomposed in accordance with formula (27). The approximated course, which is the approximated smooth function with a reconstructed or error-remedied overall mean value, and which is denoted by $\vec{a}_{fit}$ below, is related to the matrix P of the basis functions of the smooth function, the partial matrix $M_P^-$ and the measurement values $\vec{a}'$ of the imaging aberration as follows:

$$\vec{a}_{fit} = P \cdot M_P^- \cdot \vec{a}' = R \cdot \vec{a}' \quad (32)$$

The matrix R, formed by multiplying the matrix P of the basis functions of the smooth function by the partial matrix $M_P^-$ in accordance with $$R := P \cdot M_P^- \quad (33)$$

is referred to as course generation matrix below.

By providing the course generation matrix R in accordance with formula (33), it is possible to carry out the formation of the approximated course of the imaging aberration with a simple multiplication of the measurement values by the matrix R:

$$\vec{a}_{fit} = R \cdot \vec{a} \quad (34)$$

Forming the matrix R and the multiplication likewise leads to a solution of the fitting problem specified in formula (18) of obtaining an approximation to the measurement values by the smooth function and the subregion functions with minimal deviation.

In this context, reference is furthermore made to the option of using the matrix R, formed once, to form approximated courses of the imaging aberration from measurement values, which are obtained with various measurements, in each case.

A further variant of the procedure which may be carried out with the evaluation device 160 comprises an interpolation and/or extrapolation, by virtue of at least one complementary value of the considered imaging aberration being formed. Such a complementary value belongs to an image point for which no measurement value of the imaging aberration is present. Forming the at least one complementary value, which may likewise be taken into account within the scope of adjusting the imaging optical unit 130, is carried out on the basis of the approximated course.

In view of the above-described method and the different configurations thereof, reference is made to the option of providing measurement values, in each case belonging to a plurality of imaging aberrations, e.g. the wavefront aberrations Z2, Z3, and Z4, at image points in disjoint subregions 151 of an image field 150 and of carrying out a dedicated separate error correction. Here, it is possible to provide corrected values, an approximated course and/or at least one complementary value for each one of the considered imaging aberrations and to carry out the adjustment of the imaging optical unit 130 on the basis thereof.

Crosstalk may also arise in view of a plurality of imaging aberrations. Here, the causes of error for offset errors of a first measured imaging aberration may also have an effect on at least a second measured imaging aberration, and so the latter may be afflicted by corresponding offset errors. By way of example, it is possible that vertical incorrect positioning of a sensor, through which offset errors are caused when measuring the wavefront aberration Z4 (cf. FIG. 4), may also lead to the occurrence of offset errors when measuring the wavefront aberration Z2 and/or Z3. Such crosstalk to the second imaging aberration (e.g. Z2 or Z3) may be suppressed by virtue of an additional correction of the second imaging aberration being carried out on the basis of an error correction of the first imaging aberration (e.g. Z4), which is carried out using an approximation as described above. By way of example, the additional correction may be carried out on the basis of coefficients $\vec{\alpha}$ of the subregion functions which are determined within the scope of the error correction of the first imaging aberration. An error correction of the second imaging aberration in accordance with the approaches above using an approximation may be carried out prior to, or after, the additional correction.

Figure 6:
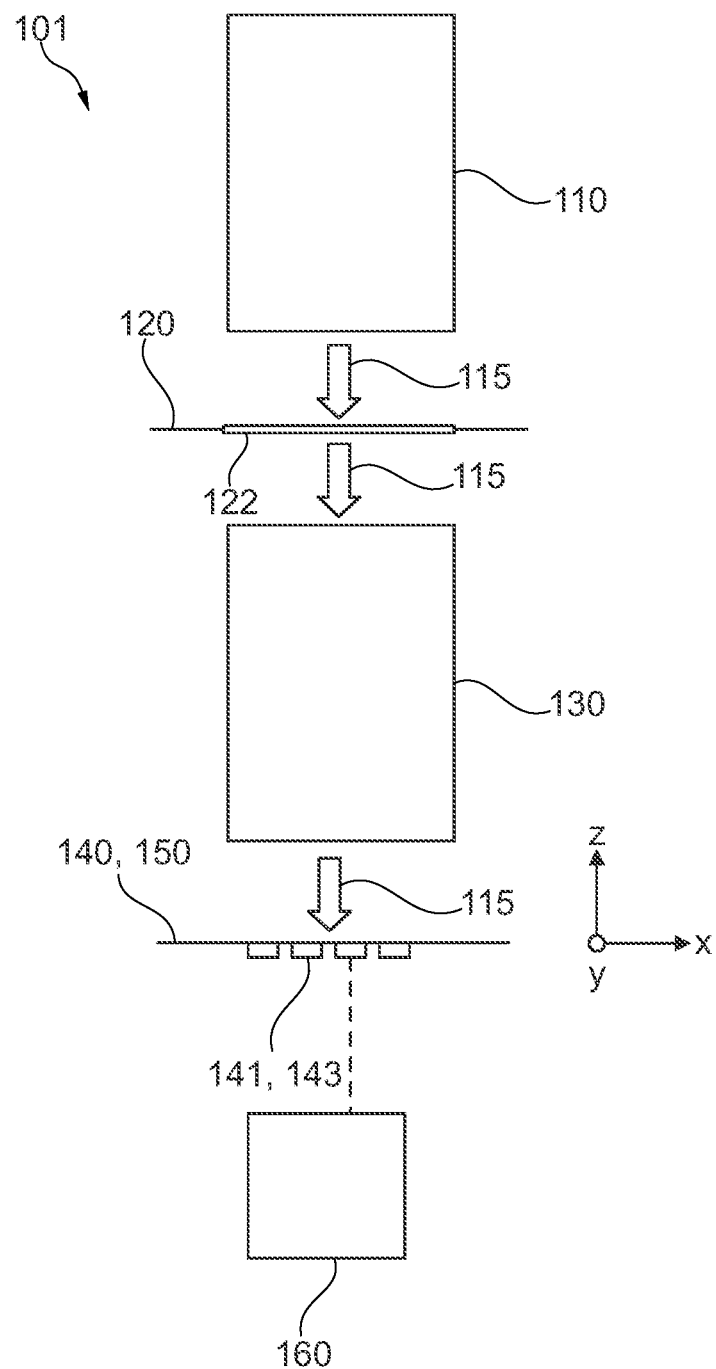
FIG. 6 shows a further optical system comprising an imaging optical unit, with which radiation transmitted through an object is able to be guided to a sensor.

Moreover, a further correction method, which will be discussed in more detail below, may be applied in relation to the system 100 and 101 of FIGS. 1, 6. Here, error-afflicted measurement values of a plurality of imaging or wavefront aberrations, which may be caused by the imaging optical unit 130, are corrected together. It is possible to use, to a large part, the same or comparable features as described above with reference to the correction of a single measured wavefront aberration. Therefore, reference is made to the description above in respect of corresponding details and aspects.

In the method, measurement values of the wavefront aberrations of interest, e.g. of the wavefront aberrations Z2, Z3 and Z4, are provided on the basis of a radiation measurement at image points in a plurality of disjoint subregions 151 of the image field 150. This is carried out with the sensor 141 having a plurality of partial sensors or with the sensor 143 arranged at different measurement positions. The measurement signals of the sensor 141 or 143 are evaluated with the associated evaluation device 160, as a result of which the measurement values of the plurality of wavefront aberrations of interest may be provided. The measurement values may have corresponding measurement errors on account of incorrect sensor positioning, which is a position error of the partial sensors in the case of the sensor 141. Error-afflicted positioning in relation to the translational degrees of freedom and rotational degrees of freedom, i.e. dx-, dy-, dz-translations and tilts or rotations in respect of the x-, y-, z-axis, may be taken into account in the method.

The method is carried out using an approximation, in which measurement values of the wavefront aberrations of interest are approximated together by a plurality of smooth functions assigned to the wavefront aberrations and by subregion functions assigned to the subregions of the image field. The smooth functions, which comprise a plurality of basis functions and which may be polynomial functions, are set in such a way that these are able to reproduce courses of the associated wavefront aberrations over the image field 150. The smooth functions or the basis functions thereof may be set with knowledge of the functionality of the imaging optical unit 130.

The subregion functions are selected in such a way that these may reproduce the influence of incorrect positioning of the sensor 141 or 143 on the measurement values of the plurality of wavefront aberrations. As a result of this, it is possible to reproduce or model actual effects of incorrect positioning on the measurement of the wavefront aberrations. By way of example, such effects are able to be determined with a measurement or simulation, e.g. by beam propagation. The subregion functions are set on the basis thereof.

With such subregion functions, it is possible within the scope of the approximation to bring about more complicated changes in the subregions 151 than merely a magnitude change by the same value, as is the case in the above-described subregion functions. By way of example, in addition to a change in the wavefront aberration Z4, a dz-translation of the employed sensor may also lead to a linear increase of the wavefront aberration Z2 over a subregion 151 of the image field 150. In this case, it is possible to use a subregion function which describes a straight line, the gradient of which depends on the sensitivity or the effect of the dz displacement of the sensor. The dz displacement of the sensor may also have an effect on other wavefront aberrations. By way of example, a cubic variation of the wavefront aberration Z3 is possible. In this case, a third-order polynomial with set coefficients may be used as subregion function. Reference is made to the fact that the specifications made above only serve for an exemplary explanation and that other or more complex relationships may be present.

Within the scope of the method for correcting a plurality of wavefront aberrations together, it is possible to carry out comparable steps as described above in relation to the correction of a single wavefront aberration. Such steps for suppressing the measurement errors which will be discussed in more detail below may also in this case be carried out with the evaluation device 160 connected to the sensor 141 or 143. The sensor 141 or 143 and the associated evaluation device 160 may, within this meaning, form an apparatus for establishing a plurality of corrected imaging aberrations. Moreover, the adjustment of the imaging optical unit 130 may be carried out on the basis of the corrected wavefront aberrations.

In the steps for the error correction described below, vectors and matrices are denoted in the same way, and reference is in part made to the same formulae, as specified above. Reference is made to the fact that, deviating from the explanations above, such components in this case relate to the plurality of wavefront aberrations, the associated plurality of smooth functions, and the subregion functions reproducing incorrect positioning. In this context, a suitable arrangement or grouping may be provided for elements contained in vectors and matrices.

For error correction purposes, corrected values $\vec{a}_{korr}$ of the plurality of wavefront aberrations may be formed, by which measurement values $\vec{a}'$ of the wavefront aberrations are replaced. This may be carried out as follows.

To this end, a function matrix M is formed from a matrix T of subregion functions and a matrix P of basis functions of the smooth functions, and the pseudoinverse $M^-$ of the function matrix M. Furthermore, a coefficient vector $\vec{c}$ belonging to the function matrix M is formed by multiplying the matrix $M^-$ by the vector $\vec{a}'$ of the measurement values of the plurality of wavefront aberrations in accordance with formula (22). This constitutes a solution to the fitting problem specified in formula (18). The coefficient $\vec{c}$ vector comprises coefficients $\vec{\alpha}$ belonging to the subregion functions and coefficients $\vec{\beta}$ belonging to the basis functions.

Moreover, the matrix T of the subregion functions is multiplied by the corresponding coefficient vector $\vec{\alpha}$ for forming a product and the product, apart from the mean value thereof, is subtracted from the vector $\vec{a}'$ of the measurement values in accordance with formula (23) in order to form the corrected values $\vec{a}_{korr}$ of the plurality of wavefront aberrations. This procedure renders it possible to correct predominantly relative differences, i.e. differences present from subregion to subregion of the image field 150, in the measurement values and avoid a uniform or global correction over all subregions.

For the common correction of the plurality of wavefront aberrations, the same variants and developments, as explained above, are available in analogous fashion.

In one possible variant of the correction procedure, subregion functions with a mean value of zero, which have a mean value of zero in relation to the image field 150, are used. In order to form such functions, the associated mean value may be subtracted from each one of the subregion functions with a mean value. This yields a unique approximation and the above-described subtraction of the mean value of the product may be implicitly contained and may thus be dispensed with.

The method may be carried out with simple polynomial basis functions, or else with orthogonalized or orthonormalized basis functions of the smooth functions. Furthermore, normalized polynomial basis functions may be used.

In a further variant carried out using subregion functions with a zero mean value, a partial matrix $M_T^-$ is formed from the provided pseudoinverse $M^-$ of the matrix M, via which partial matrix coefficients $\vec{a}$ of the subregion functions are generable. Furthermore, a correction matrix S is formed by virtue of the product of the matrix T of the subregion functions with a zero mean value and of the partial matrix $M_T^-$ being subtracted from the identity matrix I in accordance with formula (30). Forming the corrected values $\vec{a}_{korr}$ of the plurality of wavefront aberrations is carried out by multiplying the matrix S by the measurement values $\vec{a}\,'$ in accordance with formula (31). This procedure likewise leads to the solution of the fitting problem in accordance with formula (18).

In a further variant, approximated courses $\vec{a}_{fit}$ of the plurality of wavefront aberrations are formed in addition, or as an alternative, to form corrected values. This facilitates an elimination of spot noise. It is possible to replace measurement values of the wavefront aberrations by the approximated courses.

In a suitable procedure for this, once again carried out using subregion functions with a zero mean value, a partial matrix $M_P^-$ is formed from the provided pseudoinverse $M^-$ of the matrix M, via which partial matrix coefficients $\vec{\beta}$ of the basis functions P of the smooth functions are generable. Furthermore, a course generation matrix R is formed by virtue of the matrix P of the basis functions of the smooth functions being multiplied by the partial matrix $M_P^-$ in accordance with formula (33). Forming the approximated courses $\vec{a}_{fit}$ of the plurality of wavefront aberrations is carried out by multiplying the matrix R by the measurement values $\vec{a}\,'$ in accordance with formula (34). This procedure likewise leads to the solution of the fitting problem of formula (18).

A further variant comprises an interpolation and/or extrapolation by virtue of at least one complementary value of at least one of the plurality of wavefront aberrations being formed, with the complementary value belonging to spatial coordinates for which no measurement value of the wavefront aberration is present. This configuration may be carried out on the basis of an approximated course of the relevant wavefront aberration.

In respect of the method for establishing a single corrected wavefront aberration and the method for establishing a plurality of corrected wavefront aberrations together, it is possible for the measurement to relate to at least one further subregion 152 of the image field 150 which overlaps with at least one of the separate, non-overlapping subregions 151 (cf., for example, FIG. 9, which is still to be discussed in more detail below).

In this context, it may be considered, for example, to form a unified subregion with common measurement values, which comprises the further subregion 152 and the at least one subregion 151 overlapping therewith. Common measurement values of the wavefront aberration or aberrations may be provided on the basis of suitable preprocessing or correction of measurement values initially obtained in the individual overlapping subregions 151, 152. By way of example, this may be carried out with a stitching method. The unified subregion and the associated measurement values may subsequently be used in the correction and approximation, in accordance with the other subregions which are disjoint therefrom. In this procedure, a corresponding subregion function is assigned to the unified subregion.

Correspondingly, it is also possible to form a plurality of unified subregions, provide common measurement values therefor, and use these in the correction and approximation. This may be considered if a plurality of further subregions 152, which overlap with other subregions 151, are present (cf. FIG. 9). In this case, it is furthermore possible that merely unified and mutually disjoint subregions are formed.

The following procedure may furthermore be considered to the extent that measurement values of the wavefront aberration or aberrations are obtained in at least one further subregion 152 of the image field 150, where the further subregion 152 overlaps with at least one of the separate and non-overlapping subregions 151. Here, the approximation is carried out with a further subregion function assigned to the further subregion 152. Depending on the configuration of the method, the further subregion function may be selected in such a way that a change of the considered wavefront aberration, in each case by the same value, is able to be caused, or incorrect sensor positioning is able to be reproduced, herewith in the relevant subregion 152 within the scope of the approximation.

Hence, there is no union of subregions. Instead, the further overlapping subregion 152 is treated like the remaining subregions 151. Therefore, there may be a double approximation in an overlap range of overlapping subregions 151, 152 or a multiple approximation in the case of more than two overlapping subregions. In the case of a plurality of further subregions 152, a plurality of further subregion functions may be used in a corresponding manner.

Which methods described above may be used with which configurations or arrangements of subregions 151, 152 of an image field 150 provided for the measurement is explained in a complementary manner below on the basis of FIGS. 8 to 10. The subregions 151, 152 may have different geometric forms such that, deviating from FIGS. 3, 4, other forms than rectangular forms may also be present, for example triangular, hexagonal or else round or circular contours, as shown in an exemplary manner in FIGS. 8 to 10.

Such forms are determined by the configuration of a sensor used for the measurement or by the detection region thereof. To the extent that use is only made of one sensor, for example the sensor 143 moved to different measurement positions, the subregions 151, 152 may all have the same contours, deviating from FIGS. 8 to 10.

Figure 8:
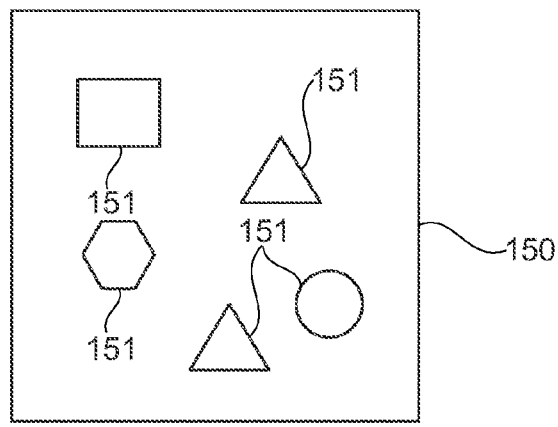
FIGS. 8 to 10 show illustrations of an image field with different arrangements of subregions.

FIG. 8 shows a measurement in which all subregions 151 of the image field 150 are disjoint. Deviating herefrom, a measurement, and hence the provision of measurement values, may additionally relate to at least one further subregion 152 of the image field 150, said further subregion overlapping with at least one of the separate, non-overlapping subregions 151. By way of example, this may be implemented with the sensor 143 arranged at different measurement positions.

Figure 9:
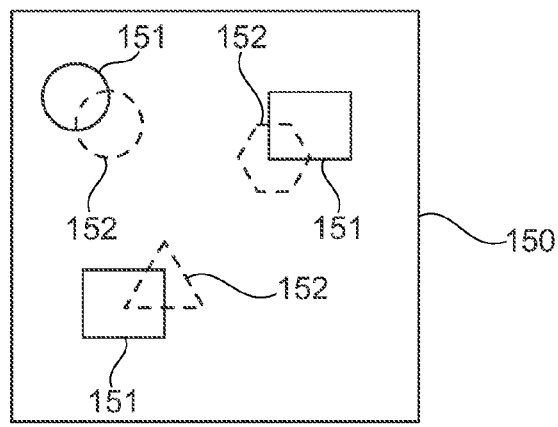

In this context, FIG. 9 depicts an exemplary measurement with six pairwise overlapping subregions 151, 152. Here, the subregions 151 depicted with full lines are disjoint in relation to one another and the further subregions 152 indicated by dashed lines are disjoint in relation to one another. The procedures explained above may be considered in the case of such a measurement. By way of example, it is possible to form three combined or unified subregions from the six pairwise overlapping subregions 151, 152, provide common measurement values for each one of the unified subregions with preprocessing, and to base the correction and approximation thereon. Here, subregion functions assigned to the unified subregions are used.

Moreover, in relation to FIG. 9, it is possible not to undertake unification but instead carry out the approximation with subregion functions assigned to the individual subregions 151, 152. Since two subregions 151, 152 are presently overlapping in each case, there is a two-fold approximation in each overlap region.

Figure 10:
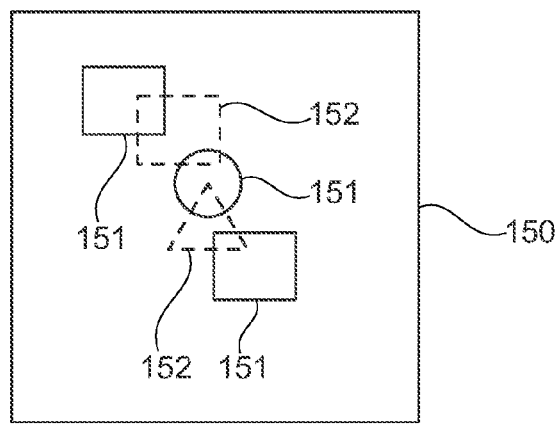

FIG. 10 depicts a further exemplary measurement with overlapping subregions 151, 152. Together, these cover a connected region of the image field 150. Here too, the subregions 151 are disjoint in relation to one another and the further subregions 152 indicated by dashed lines are disjoint in relation to one another. In these circumstances, it is likewise possible to consider the method procedure of carrying out the approximation with subregion functions assigned to the individual subregions 151, 152.

The embodiments explained above represent preferred or exemplary embodiments of the invention. Moreover, further embodiments, which may comprise further developments and/or combinations of features, are conceivable.

By way of example, with the approaches described above, it is possible to correct error-afflicted measurement values of a different individual variable of interest, which is dependent on at least one parameter. The associated parameter range may or may not represent an image field. A measurement is carried out in a corresponding manner in order to provide, on the basis thereof, measurement values of the variable in a plurality of subregions of the parameter range. A correction is carried out using an approximation, in which measurement values of the variable are approximated by a smooth function reproducing the course of the variable in the parameter range and by subregion functions assigned to the subregions of the parameter range. The subregion functions are selected in such a way that, within the approximation, an individual change of the variable is able to be caused in the subregions of the parameter range. The correction may relate to forming corrected values of the variable, an approximated course of the variable and/or at least one complementary value of the variable.

A possible example for another variable is a distortion variable, with which a distortion occurring in an image field may be reproduced. By carrying out the method, it is possible to correct error-afflicted measurement values of the distortion variable, said measurement values being obtained in a plurality of, or disjoint, subregions of the image field. By way of example, this comprises forming corrected values of the distortion variable for replacing measurement values. Moreover, a reconstruction of the distortion over the whole image field is possible. By way of example, this can be carried out by forming an approximated course and/or forming complementary values for interpolation and extrapolation.

Instead of an optical variable, it is also possible to measure a different variable in subregions of a parameter range and to correct it in accordance with the approaches described above. By way of example, this includes a measured height or a measured height profile of a test object. Here, it is possible to consider providing measurement values of the height in disjoint subregions of a two-dimensional image field and correcting measurement errors as specified above. By way of example, measurement may be carried out with an atomic force microscope or with a surface interferometer.

Depending on the respective measurement-error-afflicted variable to be corrected, the associated parameter range may, additionally or alternatively, also have one or more parameters that are not spatial coordinates. By way of example, the at least one parameter on which the variable is dependent may also be time. A further example is a parameter range comprising a time and at least one spatial coordinate.

A further possible development in relation to the method for establishing a single corrected variable consists of correcting other measurement errors, which occur individually within subregions of a parameter range, instead of offset errors. To this end, use is made of suitable subregion functions, with which a falsification of the measured variable by such measurement errors may be reproduced in the subregions of the parameter range.

LIST OF REFERENCE SIGNS

100, 101 System
110 Illumination system
115 Radiation
120 Object plane
121, 122 Object, reticle
130 Imaging optical unit
140 Image plane
141, 143 Sensor
145 Intended measurement position
150 Image field
151, 152 Subregion
160 Evaluation device
165 Distortion
dx, dy, dz Deviation
x, y, z Spatial coordinate
Z2, Z3, Z4 Wavefront aberration
$Z_s$ Actual wavefront aberration
$Z_m$ Measured wavefront aberration
$Z_r$ Reconstructed wavefront aberration

What is claimed is:

1. A method for establishing a corrected variable (Z2, Z3, Z4) which depends on at least one parameter (x, y), in a parameter range of the at least one parameter comprising:
    carrying out a measurement, wherein measurement values of the variable (Z2, Z3, Z4) are provided in a plurality of separate and non-overlapping subregions of the parameter range; and
    carrying out a measurement value correction of the variable (Z2, Z3, Z4) using an approximation in which the measurement values of the variable (Z2, Z3, Z4) are approximated by a smooth function and by subregion functions assigned to the subregions of the parameter range,
    wherein the variable is an optical variable, wherein the measurement is a radiation measurement carried out with a spatially resolving sensor, and wherein the spatially resolving sensor is arranged at different measurement positions or the spatially resolving sensor comprises a plurality of partial sensors,
    wherein a course of the variable (Z2, Z3, Z4) is reproducible over the parameter range with the smooth function, and
    wherein an individual change of the variable (Z2, Z3, Z4) is able to be caused in the subregions of the parameter range with the subregion functions.

2. The method according to claim 1, wherein the at least one parameter is a spatial coordinate (x, y).

3. The method according to claim 1, wherein the parameter range represents an image field.

4. The method according to claim 1, wherein, with the subregion functions, the variable (Z2, Z3, Z4) is changeable by the same value in the associated subregions in each case.

5. The method according to claim 1,
wherein the correction comprises forming corrected values of the variable (Z2, Z3, Z4).

6. The method according to claim 1,
wherein the approximation comprises determining coefficients of the subregion functions and wherein measurement values of the variable (Z2, Z3, Z4) are corrected using the coefficients of the subregion functions.

7. The method according to claim 1,
wherein the approximation comprises:
forming a function matrix from the subregion functions and basis functions of the smooth function;
forming the pseudoinverse of the function matrix; and
multiplying the pseudoinverse of the function matrix by a vector of measurement values of the variable (Z2, Z3, Z4) to form a coefficient vector comprising coefficients of the subregion functions and coefficients of the basis functions of the smooth function.

8. The method according to claim 7,
wherein the correction comprises:
multiplying a matrix of the subregion functions by a vector of coefficients of the subregion functions, to form a product; and
subtracting the product, apart from the mean value thereof, from the vector of measurement values of the variable (Z2, Z3, Z4).

9. The method according to claim 1,
wherein the subregion functions comprise subregion functions with a zero mean value.

10. The method according to claim 1,
wherein the approximation and correction comprises:
forming a function matrix from the subregion functions and basis functions of the smooth function;
forming a pseudoinverse of the function matrix;
forming a partial matrix from the pseudoinverse of the function matrix, from which coefficients of the subregion functions are generable;
multiplying a matrix of subregion functions by the partial matrix to form a product;
subtracting the product from an identity matrix to form a correction matrix; and
multiplying the correction matrix by a vector of measurement values of the variable (Z2, Z3, Z4).

11. The method according to claim 1,
wherein the measurement value correction comprises forming an approximated course of the variable (Z2, Z3, Z4).

12. The method according to claim 1,
wherein the measurement value correction comprises forming at least one complementary value of the variable (Z2, Z3, Z4), wherein the complementary value of the variable belongs to a value of the at least one parameter for which no measurement value of the variable (Z2, Z3, Z4) is available.

13. The method according to claim 1,
wherein the approximation and measurement value correction comprises:
forming a function matrix from the subregion functions and basis functions of the smooth function;
forming a pseudoinverse of the function matrix;
forming a partial matrix from the pseudoinverse of the function matrix, from which coefficients of the basis functions of the smooth function are generable;
multiplying a matrix of basis functions of the smooth function by the partial matrix to form a course generation matrix; and
multiplying the course generation matrix by a vector of measurement values of the variable (Z2, Z3, Z4).

14. The method according to claim 1,
wherein the measurement values of the variable (Z2, Z3, Z4) are provided in at least one further subregion of the parameter range, wherein the further subregion overlaps with at least one of the separate and non-overlapping subregions, and wherein the approximation is carried out with a further subregion function assigned to the further subregion, with which further subregion function an individual change of the variable (Z2, Z3, Z4) is able to be caused in the further subregion of the parameter range.

15. The method according to claim 1,
wherein the variable additionally comprises a further variable selected from the following group:
a distortion variable;
a wavefront aberration; and
a coefficient for a Zernike polynomial of a wavefront expansion.

16. A method for adjusting an imaging optical unit of an optical system, comprising:
performing the method as claimed in claim 1, for establishing a corrected optical variable (Z2, Z3, Z4) using a spatially resolving sensor, which is configured to be irradiated by radiation from the imaging optical unit, and
adjusting the imaging optical unit in accordance with the corrected optical variable (Z2, Z3, Z4).

17. An apparatus for establishing a corrected variable (Z2, Z3, Z4) which depends on at least one parameter (x, y), in a parameter range of the at least one parameter (x, y), comprising:
a measuring device configured to provide measurement values of the variable (Z2, Z3, Z4) in a plurality of separate and non-overlapping subregions of the parameter range; and
an evaluation device programmed to correct measurement values of the variable (Z2, Z3, Z4), wherein the evaluation device is programmed to carry out the correction using an approximation, in which the measurement values of the variable (Z2, Z3, Z4) are approximated by a smooth function and by subregion functions assigned to the subregions,
wherein the variable is an optical variable, wherein the measurement is a radiation measurement carried out with a spatially resolving sensor, and wherein the spatially resolving sensor is arranged at different measurement positions or the spatially resolving sensor comprises a plurality of partial sensors,
wherein a course of the variable (Z2, Z3, Z4) is reproduced over the parameter range with the smooth function, and
wherein an individual change of the variable (Z2, Z3, Z4) is effected in the subregions of the parameter range with the subregion functions.

18. A method for establishing a plurality of corrected wavefront aberrations (Z2, Z3, Z4) which depend on two spatial coordinates (x, y), in an image field, comprising:
performing a radiation measurement with a spatially resolving sensor, wherein measurement values of the plurality of wavefront aberrations (Z2, Z3, Z4) are provided in a plurality of separate and non-overlapping subregions of the image field; and
performing a common correction of the measurement values of the plurality of wavefront aberrations (Z2, Z3, Z4) using an approximation, in which the measurement values of the wavefront aberrations (Z2, Z3, Z4) are approximated by a plurality of smooth functions assigned to the wavefront aberrations (Z2, Z3, Z4) and by subregion functions assigned to the subregions of the image field, wherein courses of the plurality of wavefront aberrations (Z2, Z3, Z4) over the image field are reproduced with the smooth functions, wherein the influence of incorrect positioning of the spatially resolving sensor on the measurement values of the plurality of wavefront aberrations (Z2, Z3, Z4) is reproduced with the subregion functions, and wherein the spatially resolving sensor is arranged at different measurement positions or wherein the spatially resolving sensor comprises a plurality of partial sensors.

19. The method according to claim 18, wherein the common correction comprises at least one of the following:

forming corrected values of the plurality of wavefront aberrations;

forming approximated courses of the plurality of wavefront aberrations; and forming at least one complementary value of at least one of the wavefront aberrations, wherein the complementary value belongs to spatial coordinates for which no measurement value of the wavefront aberration is available.

* * * * *

UNITED STATES PATENT AND TRADEMARK OFFICE
CERTIFICATE OF CORRECTION

Page 1 of 2

PATENT NO. : 9,841,685 B2
APPLICATION NO. : 15/353406
DATED : December 12, 2017
INVENTOR(S) : Christoph Petri et al.

It is certified that error appears in the above-identified patent and that said Letters Patent is hereby corrected as shown below:

In the Specification

In Column 22, Line 39, delete "$x_1$" and insert -- $x_i$ --, therefor.

In Column 23, Lines 5-8, delete "$\vec{x} := \begin{pmatrix} x_1 \\ x_2 \\ \vdots \\ x_N \end{pmatrix}, \vec{y} := \begin{pmatrix} y_1 \\ y_2 \\ \vdots \\ y_N \end{pmatrix}$" and insert -- $\vec{x} = \begin{pmatrix} x_1 \\ x_2 \\ \vdots \\ x_N \end{pmatrix}, \vec{y} = \begin{pmatrix} y_1 \\ y_2 \\ \vdots \\ y_N \end{pmatrix}$ --, therefor.

In Column 23, Lines 29-30, delete "$\vec{a}, \vec{a}$" and insert -- $\vec{f}, \vec{g}$ --, therefor.

In Column 24, Lines 19-23, after "$\begin{cases} 1, (x_i, y_i) \in F_i \\ 0, \text{else} \end{cases}$" insert -- } --.

In Column 25, Line 4, delete "$T := (\vec{t}_1\ \vec{t}_1 \ldots \vec{t}_1)$" and insert -- $T := (\vec{t}_1\ \vec{t}_2 \ldots \vec{t}_n)$ --, therefor.

In Column 25, Line 8, delete "$P : (\vec{p}_{0,0}$" and insert -- $P := (\vec{p}_{0,0}$ --, therefor.

In Column 25, Line 19, delete "$\|M \cdot \vec{a} - \vec{a}\|^2 = \text{minimal}$" and insert -- $\|M \cdot \vec{c} - \vec{a}'\|^2 = \text{minimal}$ --, therefor.

In Column 26, Line 24, delete "$\vec{a}_{korr} = \vec{a} =$" and insert -- $\vec{a}_{korr} = \vec{a}'$ -- --, therefor.

In Column 27, Line 60, delete "$< \vec{t}_1$" and insert -- $< \vec{t}_l >$ --, therefor.

In Column 27, Line 64, delete "$\vec{a}$," and insert -- $\vec{c}$, --, therefor.

Signed and Sealed this
Twenty-ninth Day of September, 2020

Andrei Iancu
*Director of the United States Patent and Trademark Office*

CERTIFICATE OF CORRECTION (continued)
U.S. Pat. No. 9,841,685 B2

In Column 28, Line 11, delete "$T = (\tilde{\vec{t}_l} \tilde{\vec{t}_l} \ldots \tilde{\vec{t}_l})$," and insert -- $T = (\tilde{\vec{t}_1} \tilde{\vec{t}_2} \ldots \tilde{\vec{t}_n})$ --, therefor.

In Column 28, Line 38, delete "M." and insert -- $M^-$. --, therefor.

In Column 28, Line 47, delete "$\vec{a}$" and insert -- $\vec{\alpha}$ --, therefor.

In Column 28, Line 64, delete "$\vec{\alpha} = \vec{a}' -$" and insert -- $\vec{\alpha} = \vec{a}' -$ --, therefor.

In Column 28, Line 67, delete "$T = (\tilde{\vec{t}_l} \tilde{\vec{t}_l} \ldots \tilde{\vec{t}_l})$," and insert -- $T = (\tilde{\vec{t}_1} \tilde{\vec{t}_2} \ldots \tilde{\vec{t}_n})$ --, therefor.

In Column 29, Line 6, after "$S := I - T \cdot M_T^-$" insert -- , --.

In Column 29, Line 14, delete "$\vec{a}_{korr} = S \cdot \vec{a}$" and insert -- $\vec{a}_{korr} = S \cdot \vec{a}'$ --, therefor.

In Column 29, Line 65, after "$R := P \cdot M_P^-$" insert -- , --.

In Column 30, Line 6, delete "$\vec{a}_{fit} = R \cdot \vec{a}$" and insert -- $\vec{a}_{fit} = R \cdot \vec{a}'$ --, therefor.

In Column 30, Line 37, delete "thereof" and insert -- thereof. --, therefor.

In Column 32, Line 36, delete "$\vec{c}$ vector" and insert -- vector $\vec{c}$ --, therefor.

In Column 33, Line 4, delete "$\vec{a}$" and insert -- $\vec{\alpha}$ --, therefor.